United States Patent [19]
Melki et al.

[11] Patent Number: 6,080,577
[45] Date of Patent: Jun. 27, 2000

[54] SURVIVAL MOTOR NEURON (SMN) GENE: A GENE FOR SPINAL MUSCULAR ATROPHY

[75] Inventors: Judith Melki; Arnold Munnich, both of Paris, France

[73] Assignee: Institut National de la Sante et de la Recherche Medicale, Paris, France

[21] Appl. No.: 08/545,196

[22] Filed: Oct. 19, 1995

[30] Foreign Application Priority Data

Oct. 19, 1994 [EP] European Pat. Off. ............... 94402353

[51] Int. Cl.[7] ........................... C12N 15/12; C12N 15/63; C12N 15/85
[52] U.S. Cl. ..................... 435/325; 435/320.1; 536/23.1; 536/23.5; 536/24.1; 536/24.31
[58] Field of Search ................... 536/23.1, 23.5, 536/24.1, 24.31; 435/320.1, 325

[56] References Cited

PUBLICATIONS

Cross et al. Nature Genetics 6 (1994) 236–244.
Das et al. J. of Biological Chemistry 260 (1985) 6240–6247.
Stratagene Product Catalog (1991) p. 66.

*Primary Examiner*—Anthony C. Caputa
*Assistant Examiner*—Robert C. Hayes
*Attorney, Agent, or Firm*—Birch, Stewart, Kolasch & Birch, LLP

[57] ABSTRACT

The present invention relates to the discovery of the human survival motor-neuron gene or SMN gene which is a chromosome 5-SMA (Spinal Muscular Atrophy) determining gene. The present invention further relates to the nucleotide sequence encoding the SMN gene and corresponding amino acid sequence, a vector containing the gene encoding the SMN protein or a DNA sequence corresponding to the gene and transformant strains containing the SMN gene or a DNA sequence corresponding to the gene.

8 Claims, 20 Drawing Sheets

Figure 1

MAMSSGGSGGGVPEQEDSVLFRRGTGQSDDSDIWDDTALIKAYDKAVAS
FKHALKNGDICETSGKPKTTPKRKPAKKNKSQKKNTAASLQQWKVGDKCSAIWSEDG
CIYPATIASIDFKRETCVVVYTGYGNREEQNLSDLLSPICEVANNIEQNAQENENES
QVSTDESENSRSPGNKSDNIKPKSAPWNSFLPPPPPMPGPRLGPGKPGLKFNGPPPP
PPPPPPHLLSCWLPPFPSGPPIIPPPPPICPDSLDDADALGSMLISWYMSGYHTGYY
MGFRQNQKEGRCSHSLN

Figure 2A

```
CGGGGCCCCACGCTGCGCACCCGCGGGTTTGCTATGGCGATGAGCAGCGGCGGCAGT
GGTGGCGGCGTCCCGGAGCAGGAGGATTCCGTGCTGTTCCGGCGCGGCACAGGCCAG
AGCGATGATTCTGACATTTGGGATGATACAGCACTGATAAAAGCATATGATAAAGCT
GTGGCTTCATTTAAGCATGCTCTAAAGAATGGTGACATTTGTGAAACTTCGGGTAAA
CCAAAAACCACACCTAAAGAAACCTGCTAAGAAGAATAAAAGCCAAAAGAAGAAT
ACTGCAGCTTCCTTACAACAGTGGAAAGTTGGGGACAAATGTTCTGCCATTTGGTCA
GAAGACGGTTGCATTTACCCAGCTACCATTGCTTCAATTGATTTTAAGAGAGAAACC
TGTGTTGTGGTTTACACTGGATATGGAAATAGAGAGGAGCAAAATCTGTCCGATCTA
CTTTCCCCAATCTGTGAAGTAGCTAATAATATAGAACAGAATGCTCAAGAGAATGAA
AATGAAAGCCAAGTTTCAACAGATGAAAGTGAGAACTCCAGGTCTCCTGGAAATAAA
TCAGATAACATCAAGCCCAAATCTGCTCCATGGAACCCCTTTCTCCCTCCACCACCC
CCCATGCCAGGGCCAAGACTGGGACCAGGAAAGCCAGGTCTAAAATTCAATGGCCCA
CCACCGCCACCGCCACCACCACCACCCCACTTACTATCATGCTGGCTGCCTCCATTT
CCTTCTGGACCACCAATAATTCCCCCACCACCTCCCATATGTCCAGATTCTCTTGAT
GATGCTGATGCTTTGGGAAGTATGTTAATTTCATGGTACATGAGTGGCTATCATACT
GGCTATTATATGGGTTTTAGACAAAATCAAAAGAAGGAAGGTGCTCACATTCCTTA
AATTAAGGAGAAATGCTGGCATAGAGCAGCACTAAATGACACCACTAAAGAAACGAT
CAGACAGATCTGGAATGTGAAGCGTTATAGAAGATAACTGGCCTCATTTCTTCAAAA
TATCAAGTGTTGGGAAAGAAAAAGGAAGTGGAATGGGTAACTCTTCTTGATTAAAA
GTTATGTAATAACCAAATGCAATGTGAAATATTTTACTGGACTCTTTTGAAAAACCA
TCTGTAAAAGACTGAGGTGGGGGTGGGAGGCCAGCACGGTGGTGAGGCAGTTGAGAA
AATTTGAATGTGGATTAGATTTTGAATGATATTGGATAATTATTGGTAATTTTATGG
CCTGTGAGAAGGGTGTTGTAGTTTATAAAGACTGTCTTAATTTGCATACTTAAGCA
TTTAGGAATGAAGTGTTAGAGTGTCTTAAAATGTTTCAAATGGTTTAACAAATGTA
TGTGAGGCGTATGTGGCAAAATGTTACAGAATCTAACTGGTGGACATGGCTGTTCAT
TGTACTGTTTTTTTCTATCTTCTATATGTTTAAAAGTATATAATAAAAATATTTAAT
TTTTTTTTAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA
```

Figure 2B

AATTTTTAAATTTTTTGTAGAGACAGGGTCTCATTATGTTGCCCAGGGTGGTGTCAA
GCTCCAGGTCTCAAGTGATCCCCCTACCTCCGCCTCCCAAAGTTGTGGGATTGTAGG
CATGAGCCACTGCAAGAAACCTTAACTGCAGCCTAATAATTGTTTTCTTTGGGATA
ACTTTTAAAGTACATTAAAAGACTATCAACTTAATTTCTGATCATATTTTGTTGAAT
AAAATAAGTAAAATGTCTTGTGAACAAATGCTTTTTAACATCCATATAAAGCTATC
TATATATAGCTATCTATATCTATATAGCTATTTTTTTAACTTCCTTTTATTTTCCT
TACAG*GGTTTTAGACAAAATCAAAAGAAGGAAGGTGCTCACATTCCTTAAATTAA
GGA*GTAAGTCTGCCAGCATTATGAAAGTGAATCTTACTTTTGTAAAACTTTATGGT
TTGTGGAAAACAAATGTTTTTGAACAGTTAAAAAGTTCAGATGTTAGAAAGTTGAAA
GGTTAATGTAAAACAATCAATATTAAAGAATTTTGATGCCAAAACTATTAGATAAAA
GGTTAATCTACATCCCTACTAGAATTCTCATACTTAACTGGTTGGTTGTGTGGAAGA
AACATACTTTCACAATAAAGAGCTTTAGGATATGATGCCATTTTATATCACTAGTAG
GCAGACCAGCAGACTTTTTTTTATTGTGATATGGGATAACCTAGGCATACTGCACTG
TACACTCTGACATATGAAGTGCTCTAGTCAAGTTTAACTGGTGTCCACAGAGGACAT
GGTTTAACTGGAATTCGTCAAGCCTCTGGTTCTAATTTCTCATTTGCAG*GAAATGC
TGGCATAGAGCAGCACTAAATGACACCACTAAAGAAACGATCAGACAGATCTGGAAT
GTGAAGCGTTATAGAAGATAACTGGCCTCATTTCTTCAAAATATCAAGTGTTGGGAA
AGAAAAAGGAAGTGGAATGGGTAACTCTTCTTGATTAAAAGTTATGTAATAACCAA
ATGCAATGTGAAATATTTTACTGGACTCTTTTGAAAAACCATCTGTAAAAGACTGAG
GTGGGGGTGGGAGGCCAGCACGGTGGTGAGGCAGTTGAGAAAATTTGAATGTGGATT
AGATTTTGAATGATATTGGATAATTATTGGTAATTTTATGGCCTGTGAGAAGGGTGT
TGTAGTTTATAAAAGACTGTCTTAATTTGCATACTTAAGCATTTAGGAATGAAGTGT
TAGAGTGTCTTAAAATGTTTCAAATGGTTTAACAAAATGTATGTGAGGCGTATGTGG
CAAAATGTTACAGAATCTAACTGGTGGACATGGCTGTTCATTGTACTGTTTTTTCT
ATCTTCTATATGTTTAAAAGTATATAATAAAAATATTTAATTT

Figure 3A

1
CGGGGCCCCACGCTGCGCATCCGCGGGTTTGCTATGGCGATGAGCAGCGGCGGCAGT
GGTGGCGGCGTCCCGGAGCAGGAGGATTCCGTGCTGTTCCGGCGCGGCACAGGCCAG
 2
*AGCGATGATTCTGACATTTGGGATGATACAGCACTGATAAAAGCATATGATAAAGC
TGTGGCTTCATTTAAGCATGCTCTAAAGAATGGTGACATTTGTGAAACTTCGGGTAA
ACCAAAAACCACACCTAAAAGAAAACCTGCTAAGAAGAATAAAAGCCAAAAGAAGAA
              3
TACTGCAGCTTCCTTACAACAG*TGGAAAGTTGGGGACAAATGTTCTGCCATTTGGT
CAGAAGACGGTTGCATTTACCCAGCTACCATTGCTTCAATTGATTTTAAGAGAGAAA
CCTGTGTTGTGGTTTACACTGGATATGGAAATAGAGAGGAGCAAAATCTGTCCGATC
                                                        4
TACTTTCCCCAATCTGTGAAGTAGCTAATAATATAGAACAGAATGCTCAAGAG*AAT
GAAAATGAAAGCCAAGTTTCAACAGATGAAAGTGAGAACTCCAGGTCTCCTGGAAAT
AAATCAGATAACATCAAGCCCAAATCTGCTCCATGGAACTCTTTTCTCCCTCCACCA
                   5
CCCCCCATGCCAGGGCCAAGACTGGGACCAGGAAAG*CCAGGTCTAAAATTCAATGG
CCCACCACCGCCACCGCCACCACCACCACCCCACTTACTATCATGCTGGCTGCCTCC
                         6
ATTTCCTTCTGGACCACCA*ATAATTCCCCCACCACCTCCCATATGTCCAGATTCTC
TTGATGATGCTGATGCTTTGGGAAGTATGTTAATTTCATGGTACATGAGTGGCTATC
                7
ATACTGGCTATTATATG*GGTTTCAGACAAAATCAAAAGAAGGAAGGTGCTCACAT
                 8
TCCTTAAATTAAGGA*GAAATGCTGGCATAGAGCAGCACTAAATGACACCACTAAAG
AAACGATCAGACAGATCTGGAATGTGAAGCGTTATAGAAGATAACTGGCCTCATTTC
TTCAAAATATCAAGTGTTGGGAAAGAAAAAGGAAGTGGAATGGGTAACTCTTCTTG
ATTAAAAGTTATGTAATAACCAAATGCAATGTGAAATATTTTACTGGACTCTTTTGA
AAAACCATCTGTAAAAGACTGGGGTGGGGGTGGGAGGCCAGCACGGTGGTGAGGCAG
TTGAGAAATTTGAATGTGGATTAGATTTTGAATGATATTGGATAATTATTGGTAAT
TTTATGGCCTGTGAGAAGGGTGTTGTAGTTTATAAAGACTGTCTTAATTTGCATAC
TTAAGCATTTAGGAATGAAGTGTTAGAGTGTCTTAAAATGTTTCAAATGGTTTAACA
AAATGTATGTGAGGCGTATGTGGCAAAATGTTACAGAATCTAACTGGTGGACATGGC
TGTTCATTGTACTGTTTTTTCTATCTTCTATATGTTTAAAAGTATATAATAAAAAT
ATTTAATTTTTTTTAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

Figure 3B

AATTTTTAAATTTTTTGTAGAGACAGGGTCTCATTATGTTGCCCAGGGTGGTGTCAA
GCTCCAGGTCTCAAGTGATCCCCCTACCTCCGCCTCCCAAAGTTGTGGGATTGTAGG
CATGAGCCACTGCAAGAAACCTTAACTGCAGCCTAATAATTGTTTTCTTTGGGATA
ACTTTTAAAGTACATTAAAAGACTATCAACTTAATTTCTGATCATATTTTGTTGAAT
AAAATAAGTAAAATGTCTTGTGAACAAAATGCTTTTTAACATCCATATAAAGCTATC
TATATATAGCTATCTATGTCTATATAGCTATTTTTTTAACTTCCTTTTATTTTCCT
TACAG*GGTTTCAGACAAAATCAAAAGAAGGAAGGTGCTCACATTCCTTAAATTAA
GGA*GTAAGTCTGCCAGCATTATGAAAGTGAATCTTACTTTTGTAAAACTTTATGGT
TTGTGGAAAACAAATGTTTTTGAACAGTTAAAAAGTTCAGATGTTAAAAAGTTGAAA
GGTTAATGTAAAACAATCAATATTAAAGAATTTTGATGCCAAAACTATTAGATAAAA
GGTTAATCTACATCCCTACTAGAATTCTCATACTTAACTGGTTGGTTATGTGGAAGA
AACATACTTTCACAATAAAGAGCTTTAGGATATGATGCCATTTTATATCACTAGTAG
GCAGACCAGCAGACTTTTTTTATTGTGATATGGGATAACCTAGGCATACTGCACTG
TACACTCTGACATATGAAGTGCTCTAGTCAAGTTTAACTGGTGTCCACAGAGGACAT
GGTTTAACTGGAATTCGTCAAGCCTCTGGTTCTAATTTCTCATTTGCAG*GAAATGC
TGGCATAGAGCAGCACTAAATGACACCACTAAAGAAACGATCAGACAGATCTGGAAT
GTGAAGCGTTATAGAAGATAACTGGCCTCATTTCTTCAAAATATCAAGTGTTGGGAA
AGAAAAAGGAAGTGGAATGGGTAACTCTTCTTGATTAAAGTTATGTAATAACCAA
ATGCAATGTGAAATATTTTACTGGACTCTTTTGAAAACCATCTGTAAAAGACTGGG
GTGGGGGTGGGAGGCCAGCACGGTGGTGAGGCAGTTGAGAAAATTTGAATGTGGATT
AGATTTTGAATGATATTGGATAATTATTGGTAATTTTATGGCCTGTGAGAAGGGTGT
TGTAGTTTATAAAAGACTGTCTTAATTTGCATACTTAAGCATTTAGGAATGAAGTGT
TAGAGTGTCTTAAAATGTTTCAAATGGTTTAACAAAATGTATGTGAGGCGTATGTGG
CAAAATGTTACAGAATCTAACTGGTGGACATGGCTGTTCATTGTACTGTTTTTTCT
ATCTTCTATATGTTTAAAAGTATATAATAAAAATATTTAATTT

ACCTGANCCCAGANGGTCAAGGCTGCAGTGAGACGAGATTGCNCCACTGCCCTCCAC
CCTGGGTGATAAGAGTGGGACCCTGTNTCAAAACATACACACACACACACACACA
CACACACACACACACACACTCTCTCTCTCTCTCTCTCTCTCTCTCTCTCTCTCTC
TCTCTCTCAAAAACACTTGGTCTGTTATTTTTNCGAATTGTCAGTCATAGTTATCT
GTTAGACCAAAGCTGNGTAAGNACATTTATTACATTGCCTCCTACAACTTCATCAGC
TAATGTATTTGCTATATAGCAATTACATATNGGNATATATTATCTTNAGGGGATGGC
CANGTNATAAAACTGTCACTGAGGAAAGGA

C272

CCTCCCACCTNAGCCTCCCCAGTAGCTAGGACTATAGGCGTGCNCCACCAAGCTCAG
CTATTTTTNNTATTTAGTAGAGACGGGGTTTCGGCANGCTTAGGCCTCGTNTCGAAC
TCCAGTGTGTGTGTGTGTGTGTGTGTGTGTGTGTGTGTGTGTGTGTGTGTGTGTA
GATATTTATTCCCCCTCCCCCTTGGAAAAGTAAGTAAGCTCCTACTAGGAATTTAAA
ACCTGCTTGATCTATATAAAGACAAACAAGGAAAGACAAACATGGGGGCAGGAAGGA
AGGCAGATC

AFM157xd10

TCGAGGTAGATTTGTATTATATCCCATGTACACACACACACACACACACACACACAC
ACACACACAGACTTAATCTGTTTACAGAAATAAAAGGAATAAAATACCGTTTCTA
CTATACACCAAAACTAGCCATCTTGAC

C161

CCCTGAGAAGGCTTCCTCCTGAGTATGCATAAACATTCACAGCTTGCATGCGTGTGT
GTGTGTGTGTGTGTGTATGTTTGCTTGCACTGTAAAAACAATTGCAACATCAACA
GAAATAAAAATTAAAGGAATAATTCTCCTCCGACTCTGCCGTTCCATCCAGTGAAAC
TCTTCATTCTGGGGTAAAGTTCCTTCAGTTCTTTCATAGATAGGTATATACTTCATA
AGTCAAACAATCAGGCTGGGTGCAGTAGCTCATGCCTGTAATCCCAGCCCTTTGGGA
GGCCGAGCTGGGCAGATCGA

C171

TCCACCCGCCTTGGCCTCCCAAAGCNCTGGGATTACAGGCGTGACTGCCGCACCCAG
CTGTAAACTGGNTTNNTAATGGTAGATTTTNAGGTATTAACAATAGATAAAAGATA
CTTTTNGGCATACTGTGTATTGGGATGGGGTTAGAACAGGTGTNCTACCCAAGACAT
TTACTTAAAATCGCCCTCGAAATGCTATGTGAGCTGTGTGTGTGTGTGTGTGTGTGT
GTGTATTAAGGAAAAGCATGAAAGTATTTATGCTTGATTTTTTTTTTNACTCATAG
CTTCATAGTGGANCAGATACATAGTCTAAATCAAAATGTTTAAACTTTTTATGTCAC
TTGCTGTC

Restriction map of the 5q13 region for EagI(Ea),SacII(SacII),SfiII(Sfi).Numbers under parenthesis indicate the restriction fragment detected by He3; Telomeric element (E Tel ),centromeric element (E cen), Centromer(Cent.),Telomere(Tel.).Probes are indicated above the restriction map.YACS are below the restriction map.

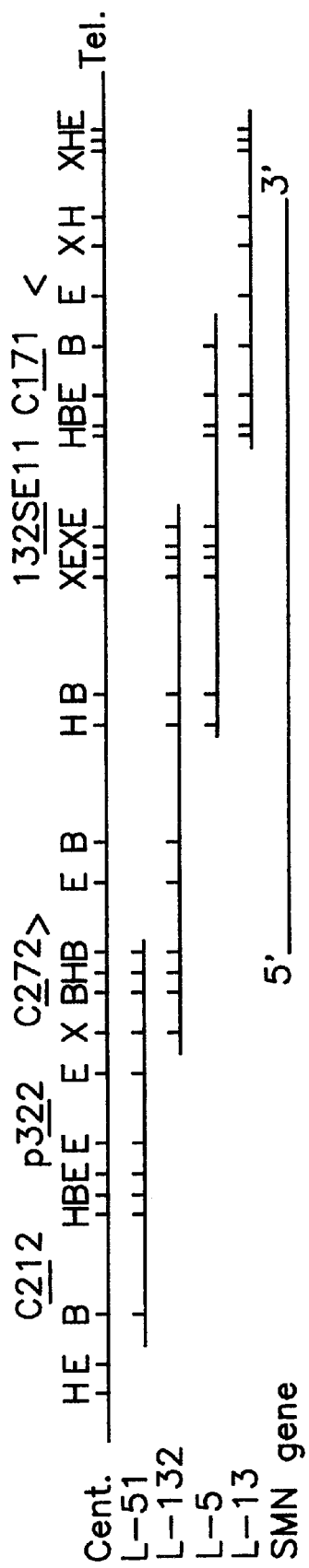

FIG.6

Telomeric element ($E^{Tel}$) containing the survival motor-neuron gene (SMN gene). Genetic map shows polymorphic markers C212, C272 and C171. Physical map shows location and direction of transcription of SMN gene; phage clones used for assembling physical map. Restriction map for EcoRI(E), XbaI(X), HindIII(H), BgIII(B), SacII(S) are shown. Cent. and Tel. indicate centromere and telomere respectively. The position of genomic rearrangements found in SMA patients are also indicated.

GENE DOSAGE ANALYSIS OF THE
5q13 REGION WITH THE 132SE11
PLASMID CONE IN SMA TYPE I
PATIENT. TOTAL HUMAN DNA FROM
SMA FAMILY WAS DIGESTED WITH
HindIII FOR SOUTHERN BLOTTING.
FILTER WAS CONSECUTIVELY
HYBRIDIZED WITH 132SE11 (A) AND
JK53 PROBES (B). A SIGNIFICANT
DECREASE IN 132SE11 BAND
INTENSITY, WHICH INDICATED THE
DELETION, COMPARED WITH THEIR
PARENTS. F/FATHER, M/MOTHER,
A/AFFECTED

Figure 8

MAMSSGGSGGGVPEQEDSVLFRRGTGQSDDSDIWDDTALIKAYDKAVASFKHALKNG
DICETSGKPKTTPKRKPAKKNKSQKKNTAASLQQWKVGDKCSAIWSEDGCIYPATIA
SIDFKRETCVVVYTGYGNREEQNLSDLLSPICEVANNIEQNAQENENESQVSTDESE
NSRSPGNKSDNIKPKSAPWNSFLPPPPPMPGPRLGPGKPGLKFNGPPPPPPPPPHL
LSCWLPPFPSGPPIIPPPPPICPDSLDDADALGSMLISWYMSGYHTGYYM

Figure 10A

1
cctcccgggcaccgtactgttccgctcccagaagccccgggcgccggaagtcgtcac
tcttaagaagggacggggccccacgctgcgcacccgcgggtttgct ATG GCG
                                                M   A
ATG AGC AGC GGC GGC AGT GGT GGC GGC GTC CCG GAG CAG GAG
 M   S   S   G   G   S   G   G   G   V   P   E   Q   E
GAT TCC GTG CTG TTC CGG CGC GGC ACA GGC CAG gtgaggtcgcagc
 D   S   V   L   F   R   R   G   T   G   Q
cagtgcagtctccctattagcgctctcagcacccttcttccggcccaactctccttc
cgca

2a
gtgtaattttgttatgtgtggattaagatgactcttggtactaacatacattttctg
attaaacctatctgnacatgagttgtttttatttcttaccctttccag AGC GAT
                                                  S   D
GAT TCT GAC ATT TGG GAT GAT ACA GCA CTG ATA AAA GCA TAT
 D   S   D   I   W   D   D   T   A   L   I   K   A   Y
GAT AAA GCT GTG GCT TCA TTT AAG gtatgaaatgcttgnttagtcgttt
 D   K   A   V   A   S   F   K
tcttattttctcgttattcatttggaaaggaattgataacatacgataaagtgttaa

2b
aggtgctttctgaggtgacggagccttgagactagcttatagtagtaactgggttat
gtcgtgacttttattctgtgcaccaccctgtaacatgtacattttttattcctatttt
cgtag CAT GCT CTA AAG AAT GGT GAC ATT TGT GAA ACT TCG GGT
       H   A   L   K   N   G   D   I   C   E   T   S   G
AAA CCA AAA ACC ACA CCT AAA AGA AAA CCT GCT AAG AAG AAT
 K   P   K   T   T   P   K   R   K   P   A   K   K   N
AAA AGC CAA AAG AAG AAT ACT GCA GCT TCC TTA CAA CAG gttat
 K   S   Q   K   K   N   T   A   A   S   L   Q   Q
tttaaaatgttgaggatttaacttcaaggatgtctcattagtccttatttaatagt
gtaaaatgtctttaact

3
gcctgcaggtcgatcaaaacgagatgatagtttgccctcttcaaaagaaatgtgtgc
atgtatatctttgatttcttttgtag TGG AAA GTT GGG GAC AAA TGT
                            W   K   V   G   D   K   C
TCT GCC ATT TGG TCA GAA GAC GGT TGC ATT TAC CCA GCT ACC
 S   A   I   W   S   E   D   G   C   I   Y   P   A   T
ATT GCT TCA ATT GAT TTT AAG AGA GAA ACC TGT GTT GTG GTT
 I   A   S   I   D   F   K   R   E   T   C   V   V   V
TAC ACT GGA TAT GGA AAT AGA GAG GAG CAA AAT CTG TCC GAT
 Y   T   G   Y   G   N   R   E   E   Q   N   L   S   D
CTA CTT TCC CCA ATC TGT GAA GTA GCT AAT AAT ATA GAA CAG
 L   L   S   P   I   C   E   V   A   N   N   I   E   Q

Figure 10B

```
AAT GCT CAA GAG gtaaggatacaaaaaaaaaaaaattcaatttctggaagcag
 N   A   Q   E
agactagatgagaaactgttaaacagtatacaca
4
ccaccgaggcattaatttttcttaatcacacccttataacaaaaacctgcatattt
tttcttttaaag AAT GAA AAT GAA AGC CAA GTT TCA ACA GAT GAA
              N   E   N   E   S   Q   V   S   T   D   E
AGT GAG AAC TCC AGG TCT CCT GGA AAT AAA TCA GAT AAC ATC
 S   E   N   S   R   S   P   G   N   K   S   D   N   I
AAG CCC AAA TCT GCT CCA TGG AAC TCT TTT CTC CCT CCA CCA
 K   P   K   S   A   P   W   N   S   F   L   P   P   P
CCC CCC ATG CCA GGG CCA AGA CTG GGA CCA GGA AAG gtaaacctt
 P   P   M   P   G   P   R   L   G   P   G   K
ctatgaaagttttccagaaaatagttaatgtcgggacatttaacctctctgttaact
aatttgtagctctccca
5
caaatattctgggtaattattttttatccttttggttttgagtccttttttattcctat
catattgaaattggtaagttaattttcctttgaaatattccttatag CCA GGT
                                                  P   G
CTA AAA TTC AAT GGC CCA CCA CCG CCA CCG CCA CCA CCA CCA
 L   K   F   N   G   P   P   P   P   P   P   P   P
CCC CAC TTA CTA TCA TGC TGG CTG CCT CCA TTT CCT TCT GGA
 P   H   L   L   S   C   W   L   P   P   F   P   S   G
CCA CCA gtaagtaaaaaagagtataggttagattttgctttcacatacaatttga
 P   P
taatta
6
ccagactttactttttgtttactggatatataaacaatatcttttctgtctccag
ATA ATT CCC CCA CCA CCT CCC ATA TGT CCA GAT TCT CTT GAT
 I   I   P   P   P   P   P   I   C   P   D   S   L   D
GAT GCT GAT GCT TTG GGA AGT ATG TTA ATT TCA TGG TAC ATG
 D   A   D   A   L   G   S   M   L   I   S   W   Y   M
AGT GGC TAT CAT ACT GGC TAT TAT ATG gtaagtaatcactcagcatct
 S   G   Y   H   T   G   Y   Y   M
ttcctgacaattttttttgtagttatgtgactttgtttggtaaatttataaaatact
acttg
7
aactgcagcctaataattgttttctttgggataacttttaaagtacattaaaagact
atcaacttaatttctgatcatattttgttgaataaaataagtaaaatgtcttgtgaa
```

Figure 10C

```
                                                                  → a
acaaaatgcttttttaacatccatatataaagctatctatatatagctatctatgtctat
                                              → T
atagctattttttttaacttcctttatttttccttacag GGT TTC AGA CAA
                                         G   F   R   Q
AAT CAA AAA GAA GGA AGG TGC TCA CAT TCC TTA AAT taaggagta
 N   Q   K   E   G   R   C   S   H   S   L   N   *
aagtctgccagcattatgaaagtgaatcttacttttgtaaaactttatggtttgtgg
                                        → g
aaaacaaatgtttttgaacagttaaaaagttcagatgttaaaaagttgaaaggttaa
tgtaaaacaatcaatattaaagaattttgatgccaaaactattagataaaaggttaa
                                        → g
tctacatccctactagaattctcatacttaactggttggttatgtggaagaaacata
ctttcacaataaagagctttaggatatgatgccattttatatcactagtaggcagac
cagcagacttttttttattgtgatatgggataacctaggcatactgcactgtacact
ctgacatatgaagtgctctagtcaagtttaactggtgtccacagaggacatggttta
                                                         8
actggaattcgtcaagcctctggttctaatttctcatttgcaggaaatgctggcata
gagcagcactaaatgacaccactaaagaaacgatcagacagatctggaatgtgaagc
gttatagaagataactggcctcatttcttcaaaatatcaagtgttgggaaagaaaaa
aggaagtggaatgggtaactcttcttgattaaaagttatgtaataaccaaatgcaat
                                                       → a
gtgaaatattttactggactcttttgaaaaaccatctagtaaaagactggggtgggg
gtgggaggccagcacggtggtgaggcagttgagaaatttgaatgtggattagattt
tgaatgatattggataattattggtaattatggcctgtgagaagggtgttgtagt
ttataaaagactgtcttaatttgcatacttaagcatttaggaatgaagtgttagagt
gtcttaaaatgtttcaatggtttaacaaaatgtatgtgaggcgtatgtggcaaaat
gttacagaatctaactggtggacatggctgttcattgtactgttttttttctatcttc
tatatgtttaaaagtatataataaaaatattta
```

Figure 11

```
gatctgccttccttcctgcccccatgtttgtctttccttgtttgtcttta    50 tatagatcaagcaggttttaaattcctagtaggagcttacatttactttt    100 ccaagggggagggggaataaatatctacacacacacacacacacacacca    150
     H4TF-1          GH
cactggagttcgagacgaggcctaagcaacatgccgaaacccgtctcta     200
                           DTF-1
ctaaatacaaaaaatagctgagcttggtggcgcacgcctatagtcctagc    250 tactggggaggctgaggtgggaggatcgcttgagcccaagaagtcgaggc    300
         Sp1
tgcagtgagccgagatcgcgccgctgcactccagcctgagcgacagggcg    350 aggctctgtctcaaaacaaacaaacaaaaaaaaaaggaaaggaaatata     400
                                  β-IFN
acacagtgaaatgaaaggattgagagaaatgaaaaatatacacgccacaa    450
                      HiNF-A
atgtgggagggcgataaccactcgtagaaagcgtgagaagttactacaag    500 cggtcctcccgggcaccgtactgttccgctcccagaagccccgggcgccg    550
                                      AP-2
gaagtcgtcactcttaagaagggacggggccccacgctgcgcacccgcgg    600
     E4F1
gtttgct ATG GCG ATG AGC AGC GGC GGC AGT GGT GGC        637
         M   A   M   S   S   G   G   S   G   G
```

Figure 12A

| | | | | | | | | | | | |
|---|---|---|---|---|---|---|---|---|---|---|---|
| cggcgtggtagcaggcc | ATG | GCG | ATG | GGC | AGT | GGC | GGA | GCG | | | 41 |
| | Met | Ala | Met | Gly | Ser | Gly | Gly | Ala | | | |

```
GGC TCC GAG CAG GAA GAT ACG GTG CTG TTC CGG CGT GGC            80
Gly Ser Glu Gln Glu Asp Thr Val Leu Phe Arg Arg Gly

ACC GGC CAG AGT GAT GAT TCT GAC ATT TGG GAT GAT ACA           119
Thr Gly Gln Ser Asp Asp Ser Asp Ile Trp Asp Asp Thr

GCA TTG ATA AAA GCT TAT GAT AAA GCT GTG GCT TCC TTT           158
Ala Leu Ile Lys Ala Tyr Asp Lys Ala Val Ala Ser Phe

AAG CAT GCT CTA AAG AAC GGT GAC ATT TGT GAA ACT CCA           197
Lys His Ala Leu Lys Asn Gly Asp Ile Cys Glu Thr Pro

GAT AAG CCA AAA GGC ACA GCC AGA AGA AAA CCT GCC AAG           236
Asp Lys Pro Lys Gly Thr Ala Arg Arg Lys Pro Ala Lys

AAG AAT AAA AGC CAA AAG AAG AAT GCC ACA ACT CCC TTG           275
Lys Asn Lys Ser Gln Lys Lys Asn Ala Thr Thr Pro Leu

AAA CAG TGG AAA GTT GGT GAC AAG TGT TCT GCT GTT TGG           314
Lys Gln Trp Lys Val Gly Asp Lys Cys Ser Ala Val Trp

TCA GAA GAC GGC TGC ATT TAC CCA GCT ACT ATT ACG TCC           353
Ser Glu Asp Gly Cys Ile Tyr Pro Ala Thr Ile Thr Ser

ATT GAC TTT AAG AGA GAA ACC TGT GTC GTG GTT TAT ACT           392
Ile Asp Phe Lys Arg Glu Thr Cys Val Val Val Tyr Thr

GGA TAT GGA AAC AGA GAG GAG CAA AAC TTA TCT GAC CTA           431
Gly Tyr Gly Asn Arg Glu Glu Gln Asn Leu Ser Asp Leu

CTT TCC CCG ACC TGT GAA GTA GCT AAT AGT ACA GAA CAG           470
Leu Ser Pro Thr Cys Glu Val Ala Asn Ser Thr Glu Gln

AAC ACT CAG GAG AAT GAA AGT CAA GTT TCC ACA GAC GAC           509
Asn Thr Gln Glu Asn Glu Ser Gln Val Ser Thr Asp Asp

AGT GAA CAC TCC TCC AGA TCG CTC AGA AGT AAA GCA CAC           548
Ser Glu His Ser Ser Arg Ser Leu Arg Ser Lys Ala His
```

Figure 12B

```
AGC AAG TCC AAA GCT GCT CCG TGG ACC TCA TTT CTT CCT     587
Ser Lys Ser Lys Ala Ala Pro Trp Thr Ser Phe Leu Pro

CCA CCA CCC CCA ATG CCA GGG TCA GGA TTA GGA CCA GGA     626
Pro Pro Pro Pro Met Pro Gly Ser Gly Leu Gly Pro Gly

AAG CCA GGT CTA AAA TTC AAC GGC CCG CCG CCG CCT         665
Lys Pro Gly Leu Lys Phe Asn Gly Pro Pro Pro Pro

CCA CTA CCC CCT CCC CCC TTC CTG CCG TGC TGG ATG CCC     704
Pro Leu Pro Pro Pro Pro Phe Leu Pro Cys Trp Met Pro

CCG TTC CCT TCA GGA CCA CCA ATA ATC CCG CCA CCC CCT     743
Pro Phe Pro Ser Gly Pro Pro Ile Ile Pro Pro Pro Pro

CCC ATC TCT CCC GAC TGT CTG GAT GAC ACT GAT GCC CTG     782
Pro Ile Ser Pro Asp Cys Leu Asp Asp Thr Asp Ala Leu

GGC AGT ATG CTA ATC TCT TGG TAC ATG AGT GGC TAC CAC     821
Gly Ser Met Leu Ile Ser Trp Tyr Met Ser Gly Tyr His

ACT GGC TAC TAT ATG GGT TTC AGA CAA AAT AAA AAA GAA     860
Thr Gly Tyr Tyr Met Gly Phe Arg Gln Asn Lys Lys Glu

GGA AAG TGC TCA CAT ACA AAT taag                        885
Gly Lys Cys Ser His Thr Asn  *
```

Figure 13

```
       20          30          40          50          60          70
GSGGGVPEQEDSVLFRRGTGQSDDSDIWDDTALIKAYDKAVASFKHALKNGDICETS
====    ====-=============-================-===-========
GSGGAGSEQEDTVLFRRGTGQSDDSDIWDDTALIKAYDKAVASFKHALKNGDICETP
            20          30          40          50          60

80          90         100         110         120         130
GKPKTTPKRKPAKKNKSQKKNTAASLQQWKVGDKCSAIWSEDGCIYPATIASIDFKR
===-= -================--- = ==========-=============-======
DKPKGTARRKPAKKNKSQKKNATTPLKQWKVGDKCSAVWSEDGCIYPATITSIDFKR
   70                  90         100         110         120

140         150         160         170         180          1
ETCVVVYTGYGNREEQNLSDLLSPICEVANNIEQNAQENENESQVSTDESENSRSPG
======================== =====  ===-====--========-== =
ETCVVVYTGYGNREEQNLSDLLSPTCEVANSTEQNTQENE--SQVSTDDSEHSSRSL
       130         140                 160         170          1

90         200         210         220         230         240
NKSDNIKPKSAPWNSFLPPPPPMPGPRLGPGKPGLKFNGPPPPPPPPPHLLSCWLP
 = =-=== ==========   ================== ===  = ==-=
RSKAHSKSKAAPWTSFLPPPPPMPGSGLGPGKPGLKFNGPPPPPPLPPPPFLPCWMP
80         190         200         210         220         230

250         260         270         280         290         300
PFPSGPPIIPPPPPICPDSLDDADALGSMLISWYMSGYHTGYYMGFRQNQKEGRCSH
==============  == ===-=========================  ===-===
PFPSGPPIIPPPPPISPDCLDDTDALGSMLISWYMSGYHTGYYMGFRQNKKEGKCSH
        240         250         260         270         280         290

SL
-
TN
```

SURVIVAL MOTOR NEURON (SMN) GENE: A GENE FOR SPINAL MUSCULAR ATROPHY

BACKGROUND OF THE INVENTION

1. Field of the Invention

The present invention relates to the discovery of the human survival motor-neuron gene or SMN gene which is a chromosome 5-SMA (Spinal Muscular Strophy) determining gene. The present invention further relates to the nucleotide sequence encoding the SMN gene and corresponding amino acid sequence, a vector containing the gene encoding the SMN protein or a DNA sequence corresponding to the gene and transformant strains containing the SMN gene or a DNA sequence corresponding to the gene.

More particularly, the present invention relates to means and methods for detecting motor neuron diseases having symptoms of muscular weakness with or without sensory changes such as amytrophic lateral sclerosis (ALS), spinal muscular atrophy (SMA), primary lateral sclerosis (PLS), arthrogryposis multiplex congenita (AMC), and the like. The methods for detecting such motor neuron diseases include, but are not limited to, the use of specific DNA primers in the PCR technique, the use of hybridization probes and the use of polyclonal and monoclonal antibodies.

Even more particularly, the present invention relates to the use of the human SMN gene or part of the gene, cDNA, oligonucleotide or the encoded protein or part thereof in therapy by insertion of the human SMN gene or part of the gene, cDNA, oligonucleotide or the encoded protein or part thereof, if required, into engineered viruses or vectors that serve as harmless carriers to transport the gene or part of the gene, cDNA, oligonucleotide or the encoded protein or part thereof to the body's cells including bone marrow cells.

The invention further relates to antigen sequences directed to the SMN gene.

In order to provide means for the therapy of motor neuron diseases, the invention also relates to the protein encoded by the SMN gene.

The present invention also relates to the isolation of the mouse SMN gene, the nucleotide sequence encoding the mouse SMN gene and corresponding amino acid sequence. A transgenic mouse model that hyperexpresses all or part of the SMN gene and a transgenic mouse model produced by homologous recombination with a mutated SMN gene is also described.

2. State of the Art

Degenerative motor neuron diseases can be placed into three major categories. Amyotrophic lateral sclerosis or ALS, motor neuron diseases such as spinal muscular atrophy (SMA) and motor neuron diseases associated with other degenerative disorders such as primary lateral sclerosis (PLS).

Amyotrophic lateral sclerosis (ALS) is the most frequently encountered form of progressive neuron disease and is characteristically a disorder of middle age. The disease is characterized by progressive loss of motor neurons, both in the cerebral cortex and in the anterior horns of the spinal cord, together with their homologues in some motor nuclei of the brainstem. It typically affects both upper and lower motor neurons, although variants may predominantly involve only particularly subsets of motor neurons, particularly early in the course of illness.

ALS is evidenced by the development of asymmetric weakness, with fatigue and cramping of affected muscles. The weakness is accompanied by visible wasting and atrophy of the muscles evolves and over time, more and more muscles become involved until the disorder takes on a symmetric distribution in all regions, including muscles of chewing, swallowing and movement of the face and tongue. Fifty percent of patients having ALS can be expected to die within three to five years for the onset of the disease. Presently, there is no treatment that has influence on the pathologic process of ALS.

Spinal muscular atrophies (SMA) are characterized by degeneration of anterior horn cells of the spinal cord leading to progressive symmetrical limb and trunk paralysis associated with muscular atrophy. SMA represents the second most common fatal, autosomal recessive disorder after cystic fibrosis (1out 6000 newborns). Childhood SMA is classically subdivided into three clinical groups on the basis of age of onset and clinical course. The acute form of Werdnig-Hoffmann disease (Type I) is characterized by sever generalized muscle weakness and hypotonia at birth or in the 3 months following birth. Death, from respiratory failure, usually occurs within the first two years. This disease may be distinguished from the intermediate (Type II) and juvenile (Type III, Kugelberg-Welander disease) forms. Type II children were able to sit but unable to stand or walk unaided, and they live beyond 4 years. Type III patients had proximal muscle weakness, starting after the age of two. The underlying biochemical defect remains unknown. In addition there is known to exist a slowly evolving adult form of SMA, sometimes referred to as SMA IV.

Primary lateral sclerosis (PLS) is a variant of ALS and occurs as a sporadic disease of late life. Neuropathologically in PLS there is a degeneration of the corticospinal (pyramidal) tracts, which appear almost normal at brainstem levels but become increasingly atrophic as they descent through the spinal column. The lower limbs are affected earliest and most severely.

Arthrogryposis Multiplex Congenita (AMC) is a frequent syndrome characterized by congenital joint fixation (incidence of 1 out of 3000 live births) resulting from decreased fetal movements in utero (Stern, W. G., JAMA, 81:1507–1510 (1923): Hall, J. G., *Clin. Orthop.,* 194:44–53 (1985)). AMC has been ascribed to either oligo-hydramnios or a variety of diseases involving the central nervous system, skeletal muscle, or spinal cord. Since neuronal degeneration and neuronophagia occur in the anterior horns, it has been hypothesized that the AMC of neurogenic origin could be related to acute spinal muscular atrophy; SMA Type I Werdnig-Hoffman disease (Banker, B. Q., *Hum. Pathol.,* (1986); 117:656–672.

The detection and clinical diagnosis for ALS, AMC, SMA and PLS is quite limited to muscle biopsies, the clinical diagnosis by a physician and electromyography (EMG). For example, the clinical criteria for diagnosing SMA is set forth in the Clinical Criteria International SMA Consortium (Munsat T. L., *Neuromuscular Disorders,* Vol. 1, p. 81 (1991)). but due to the complications of the various tests to detect motor neuron disorders, the clinician usually attempts to eliminate various categories of other disease states such as structural lesions, infections, intoxications, metabolic disorders and heriditary biochemical disorders prior to utilizing the above-described test methods.

Presently there is no treatment for any of the above-mentioned motor neuron disorders. Basic rehabilitative measures, including mechanical aids of various kinds, may help patients that have these diseases overcome the effects of their disabilities, but often confining respiratory support systems are necessary to have the patient survive longer.

Accordingly, it is an object of the present invention to characterize the SMN gene which is responsible for SMA disorders and to clone the SMN gene into a vector, for example a plasmid, a cosmid, a phage, a YAC vector, that can be used in the transformation process to produce large quantities of the SMN gene and SMN protein.

In yet another aspect of the invention is the use of primers and hybridization probes to detect and diagnose patients having motor neuron disorders such as AMC, ALS, SMA and PLS. Yet another aspect of the present invention is the use of SMN gene or part thereof or cDNA, oligonucleotides, protein or part thereof in therapy to correct disorders present in, for example AMC, SMA, ALS and PLS patients, especially gene disorders.

In yet another aspect, the present invention provides monoclonal and polyclonal antibodies for detection of SMN gene defects in SMA patients.

Another object of the present invention provides the characterization of the SMN gene in the mouse. A transgenic mouse model is presented that hyperexpresses all or part of the SMN gene or a transgenic mouse that by homologous recombination with a mutated mouse SMN gene produces abnormalities in the SMN gene is also described.

According to a further aspect of the invention, the therapy of motor neuron diseases can involve the protein encoded by the SMN gene.

These and other objects are achieved by the present invention as evidenced by the summary of the invention, the description of the preferred embodiments and the claims.

OBJECTS AND SUMMARY OF THE INVENTION

It is an object of the present invention to provide a novel human Survival Motor Neuron gene or SMN gene, its DNA sequence and amino acid sequence.

Another aspect of the present invention provides a novel mouse Survival Motor Neuron gene or SMN gene, its DNA sequence and amino acid sequence.

Yet another aspect of the present invention is the provision of a vector which is capable of replicating in a host microorganism to provide large quantities of the human or mouse SMN protein.

Yet another aspect of the present invention is the provision of specific DNA sequences that can be used to detect and diagnose spinal muscular atrophy and other motor neuron disorders. These DNA sequences can be used as primers in the polymerase chain reaction to amplify and detect the SMN gene sequence, a truncated or mutated version of the SMN gene sequence or lack of said sequence which leads to the diagnosis of SMA, AMC, and other motor neuron disorders.

Yet another aspect of the present invention provides a transgenic mouse that hyperexpresses all or part of the SMN gene or a transgenic mouse that by homologous recombination with a mutated mouse SMN gene produces abnormalities in the SMN gene is also described.

The inventors have identified two genes respectively designated T-BCD541 and C-BCD541, which are involved in motor neuron disorders.

The T-BCD541 gene is responsible for the motor neuron diseases of the SMA type, since its alteration either by partial or total deletion, by mutation or any other modification, is sufficient to lead to a pathological state at the clinical electromyographic or muscle morphological levels.

The C-BCD541 gene is different from the T-BCD541 gene, at the level of the cDNA, since two nucleotides are modified. This C-BCD541 gene is nevertheless not correctly processed during the transcription in controls and patients suffering from motor neuron diseases. The genomic DNA of the C-BCD541 gene is not correctly spliced during the transcription providing thus for an abnormal transcript. The difference between the splicing of the T-BCD541 and the C-BCD541 gene results from differences in the sequence of the introns of these genes.

The present invention thus further characterizes the structure and organization of the human SMN gene which was found to be approximately 20 kb in length and consists of 9 exons interrupted by 8 introns. The nucleotide sequence, amino acid sequence as well as the exon-intron boundaries of the human SMN gene is set forth in FIG. 10. All exon-intron boundaries display the consensus sequence found in other human genes. A polyadenylation consensus site is localized about 550 bp downstream from the stop condon (FIG. 10). The entire intron/exon structure of the SMN gene permits the characterizations of the SMN gene mutations in SMA disease or other motor neuron diseases.

The present invention also defines means for the detection of genomic abnormalities relating to motor neutron diseases at the level of the T-BCD541 gene or at the level of the C-BCD541 gene.

The genes of the invention can be further defined in that each of them comprise intronic sequences corresponding to the following sequences:

```
In the T-BCD541 gene
- for intron n° 6:

5' AATTTTTAAATTTTTTGTAGAGACAGGGTCTCATTATGTTGCCCAGGGTG

GTGTCAAGCTCCAGGTCTCAAGTGATCCCCCTACCTCCGCCTCCCAAAGTTGT

GGGATTGTAGGCATGAGCCACTGCAAGAAAACCTTAACTGCAGCCTAATAATT

GTTTTCTTTGGGATAACTTTTAAAGTACATTAAAAGACTATCAACTTAATTTC

TGATCATATTTTGTTGAATAAAATAAGTAAAATGTCTTGTGAACAAAATGCTT

TTTAACATCCATATAAAGCTATCTATATATAGCTATCTATGTCTATATAGCTA

TTTTTTTTAACTTCCTTTTATTTTCCTTACAG 3' (SEQ ID NO:1)

- for intron n° 7:

5' GTAAGTCTGCCAGCATTATGAAAGTGAATCTTACTTTTGTAAAACTTTAT

GGTTTGTGGAAAACAAATGTTTTTGAACAGTTAAAAAGTTCAGATGTTAAAAA

GTTGAAAGGTTAATGTAAAACAATCAATATTAAAGAATTTTGATGCCAAAACT

ATTAGATAAAAGGTTAATCTACATCCCTACTAGAATTCTCATACTTAACTGGT

TGGTTATGTGGAAGAAACATACTTTCACAATAAAGAGCTTTAGGATATGATGC

CATTTTATATCACTAGTAGGCAGACCAGCAGACTTTTTTTTATTGTGATATGG

GATAACCTAGGCATACTGCACTGTACACTCTGACATATGAAGTGCTCTAGTCA

AGTTTAACTGGTGTCCACAGAGGACATGGTTTAACTGGAATTCGTCAAGCCTC

TGGTTCTAATTTCTCATTTGCAG 3' (SEQ ID NO:2)

In the C-BCD541 gene:
- for intron n° 6:

AATTTTTAAATTTTTTGTAGAGACAGGGTCTCATTATGTTGCCCAGGGTGGTGTCAAGCTCCA

GGTCTCAAGTGATCCCCCTACCTCCGCCTCCCAAAGTTGTGGGATTGTAGGCATGAGCCACTG

CAAGAAAACCTTAACTGCAGCCTAATAATTGTTTTCTTTGGGATAACTTTTAAAGTACATTAA

AAGACTATCAACTTAATTTCTGATCATATTTTGTTGAATAAAATAAGTAAAATGTCTTGTGAA

CAAAATGCTTTTTAACATCCATATAAAGCTATCTATATATAGCTATCTATATCTATATAGCTA

TTTTTTTTAACTTCCTTTTATTTTCCTTACAG* (SEQ ID NO:3)

- for intron n° 7:

*GTAAGTCTGCCAGCATTATGAAAGTGAATCTTACTTTT

GTAAAACTTTATGGTTTGTGGAAAACAAATGTTTTTGAACAGTTAAAAAGTTCAGATGTTAGA

AAGTTGAAAGGTTAATGTAAAACAATCAATATTAAAGAATTTTGATGCCAAAACTATTAGATA

AAAGGTTAATCTACATCCCTACTAGAATTCTCATACTTAACTGGTTGGTTGTGTGGAAGAAAC

ATACTTTCACAATAAAGAGCTTTAGGATATGATGCCATTTTATATCACTAGTAGGCAGACCAG

CAGACTTTTTTTTATTGTGATATGGGATAACCTAGGCATACTGCACTGTACACTCTGACATAT

GAAGTGCTCTAGTCAAGTTTAACTGGTGTCCACAGAGGACATGGTTTAACTGGAATTCGTCAA

GCCTCTGGTTCTAATTTCTCATTTGCAG* (SEQ ID NO:4)
```

In a preferred embodiment of the invention, the gene of the invention is capable of hybridizing in stringent conditions with the sequence of FIG. 3 (SEQ ID NOS: 12–13) used as probe.

As hereabove written, the invention further relates to a variant of the SMN gene, which variant is a C-BCD541 gene having a cDNA sequence corresponding to the sequence of FIG. 2 (SEQ ID NOS: 10–11).

The invention also relates to cDNA sequences such as obtained from one of the above genes. Such cDNA sequences are disclosed in FIGS. 2 and 3. Both of these cDNA sequence are capable of encoding a protein comprising the amino acid sequence described in FIG. 1 (SEQ ID NO: 9).

Despite this capacity to encode for such a protein, the inventors have noted that the C-BCD541 gene is not able to produce in vivo this protein or is not able to produce it in a sufficient quantity due to the abnormal splicing of the gene during the transcription. Thus, the presence of the C-BCD541 gene does not enable to correct in vivo the deficiency (deletion, mutation, . . . ) of the T-BCD541 gene responsible for the motor neuron diseases of the SMA type or other motor neuron disorders.

In a particular embodiment, the invention relates also to a nucleotide sequence comprising nucleotides 34 to 915 of the sequence of FIG. 3, or to a sequence comprising nucleotides 34 to 915 of the sequence of FIG. 2.

These nucleotide sequences correspond to the coding sequence of respectively the T-BCD541 gene and C-BCD541 gene.

The introns of the hereabove described genes are also included in the application. Especially introns 6 and 7 have respectively the following sequences:

```
For the T-BCD541 gene:
- Intron 6:

5' AATTTTTAAATTTTTTGTAGAGACAGGGTCTCATTATGTTGCCCAGGGTG

GTGTCAAGCTCCAGGTCTCAAGTGATCCCCCTACCTCCGCCTCCCAAAGTTGT

GGGATTGTAGGCATGAGCCACTGCAAGAAAACCTTAACTGCAGCCTAATAATT

GTTTTCTTTGGGATAACTTTTAAAGTACATTAAAAGACTATCAACTTAATTTC

TGATCATATTTTGTTGAATAAAATAAGTAAAATGTCTTGTGAACAAAATGCTT

TTTAACATCCATATAAAGCTATCTATATATAGCTATCTATGTCTATATAGCTA

TTTTTTTTAACTTCCTTTTATTTTCCTTACAG 3'  (SEQ ID NO:1)

- Intron 7:

5' GTAAGTCTGCCAGCATTATGAAAGTGAATCTTACTTTTGTAAAACTTTAT

GGTTTGTGGAAAACAAATGTTTTTGAACAGTTAAAAAGTTCAGATGTTAAAAA

GTTGAAAGGTTAATGTAAAACAATCAATATTAAAGAATTTTGATGCCAAAACT

ATTAGATAAAAGGTTAATCTACATCCCTACTAGAATTCTCATACTTAACTGGT

TGGTTATGTGGAAGAAACATACTTTCACAATAAAGAGCTTTAGGATATGATGC

CATTTTATATCACTAGTAGGCAGACCAGCAGACTTTTTTTTATTGTGATATGG

GATAACCTAGGCATACTGCACTGTACACTCTGACATATGAAGTGCTCTAGTCA

AGTTTAACTGGTGTCCACAGAGGACATGGTTTAACTGGAATTCGTCAAGCCTC

TGGTTCTAATTTCTCATTTGCAG 3' (SEQ ID NO:2)

For the C-BCD541 gene:
- Intron 6:

AATTTTTAAATTTTTTGTAGAGACAGGGTCTCATTATGTTGCCCAGGGTGGTGTCAAGCTCCA

GGTCTCAAGTGATCCCCCTACCTCCGCCTCCCAAAGTTGTGGGATTGTAGGCATGAGCCACTG

CAAGAAAACCTTAACTGCAGCCTAATAATTGTTTTCTTTGGGATAACTTTTAAAGTACATTAA

AAGACTATCAACTTAATTTCTGATCATATTTTGTTGAATAAAATAAGTAAAATGTCTTGTGAA

CAAAATGCTTTTTAACATCCATATAAAGCTATCTATATATAGCTATCTATĀTCTATATAGCTA

TTTTTTTTAACTTCCTTTTATTTTCCTTACAG*  (SEQ ID NO:3)

- Intron 7:

_GTAAGTCTGCCAGCATTATGAAAGTGAATCTTACTTTT

GTAAAACTTTATGGTTTGTGGAAAACAAATGTTTTTGAACAGTTAAAAAGTTCAGATGTTAḠA

AAGTTGAAAGGTTAATGTAAAACAATCAATATTAAAGAATTTTGATGCCAAAACTATTAGATA

AAAGGTTAATCTACATCCCTACTAGAATTCTCATACTTAACTGGTTGGTTḠTGTGGAAGAAAC
```

-continued

```
ATACTTTCACAATAAAGAGCTTTAGGATATGATGCCATTTTATATCACTAGTAGGCAGACCAG

CAGACTTTTTTTTATTGTGATATGGGATAACCTAGGCATACTGCACTGTACACTCTGACATAT

GAAGTGCTCTAGTCAAGTTTAACTGGTGTCCACAGAGGACATGGTTTAACTGGAATTCGTCAA

GCCTCTGGTTCTAATTTCTCATTTGCAG*  (SEQ ID NO:4)
```

The invention further encompasses a nucleotide sequence, characterized in that it comprises at least round 9 nucleotides and in that it is comprised within a sequence which has been described above or in that it hybridizes with a sequence as described above in hybridization conditions which are determined after choosing the oligonucleotide.

For the determination of the hybridization conditions, reference is made to the hybridization techniques for oligonucleotides probes such as disclosed in Sambrook et al, *Molecular Cloning, a Laboratory Manual*, 2nd edition, 1989.

The sequences of the invention are either DNA (especially genomic DNA or cDNA or synthetic DNA) or RNA. They can be used as probes for the detection of the T-BCD541 or C-BCD541 genes or as primers for the amplification of genomic DNA present in a biological sample.

Preferred primers are those comprising or relating to the following sequences:

```
                                        (SEQ ID NO:5)
a)    5'  AGACTATCAACTTAATTTCTGATCA  3'  (R 111)

(SEQ ID NO:6)
b)    5'  TAAGGAATGTGAGCACCTTCCTTC   3'  (541C770)
```

The above primers are characteristic of exon 7 of the T-BCD541 gene.

```
                                        (SEQ ID NO:7)
(c)   GTAATAACCAAATGCAATGTGAA       (541C960)

(SEQ ID NO:8)
(d)   CTACAACACCCTTCTCACAG          (541C1120)
```

The above primers are characteristic of exon 8 of the T-BCD541 gene.

The primers used by pairs can form sets for the amplification of genomic DNA in order to detect motor neuron diseases.

Inverted complementary sequences with respect to the above primers can also be used.

Preferred sets of primers are the following:

a pair of primers contained in the sequence comprising nucleotides 921 to 1469 of the sequence of FIG. 3 and/or a pair of primers comprising the following sequences:

```
5'  AGACTATCAACTTAATTTCTGATCA  3'  (SEQ ID NO:5)

5'  TAAGGAATGTGAGCACCTTCCTTC   3'  (SEQ ID NO:6)
```

Another preferred set of primers comprises:

a pair of primers having the following sequences:

```
5'  AGACTATCAACTTAATTTCTGATCA  3'  (SEQ ID NO:5)

5'  TAAGGAATGTGAGCACCTTCCTTC   3'  (SEQ ID NO:6)
``` a pair of primers having the following sequences:

```
5'  GTAATAACCAAATGCAATGTGAA    3'  (SEQ ID NO:7)

and/or

5'  CTACAACACCCTTCTCACAG       3'  (SEQ ID NO:6)
```

From a general point of view for the detection of divergence in exon 7, between the T-BCD541 and C-BCD541 genes oligonucloetide primers can be selected in the fragment 5' from the divergence and within exon 7 or intron 7.

Other primers that can be used for SSCP analysis for diagnostic purposes are selected from amongst the following:

```
5'EXON 1 121md/121me    Size: 170 bp

121MD       5'  AGG GCG AGG CTC TGT CTC A        (SEQ ID NO:24)

121ME       5'  CGG GAG GAC CGC TTG TAG T        (SEQ ID NO:25)

EXON1    121ma/121mf    Size: 180 bp

121MA       5'  GCC GGA AGT CGT CAC TCT T        (SEQ ID NO:26)

121MF       5'  GGG TGC TGA GAG CGC TAA TA       (SEQ ID NO:27)

EXON2A   ex2A5/Ex2A3    Size: 242 bp
```

-continued

| | | | |
|---|---|---|---|
| EX2A5 | 5' | TGT GTG GAT TAA GAT GAC TC | (SEQ ID NO:28) |
| EX2A3 | 5' | CAC TTT ATC GTA TGT TAT C | (SEQ ID NO:29) |

EXON2B  Ex2B5/EX23   Size: 215 bp

| | | | |
|---|---|---|---|
| EX2B5 | 5' | CTG TGC ACC ACC CTG TAA CAT G | (SEQ ID NO:30) |
| EX23 | 5' | AAG GAC TAA TGA GAC ATC C | (SEQ ID NO:31) |

EXON3  SM8C/161CR2   Size: 238 bp

| | | | |
|---|---|---|---|
| SM8C | 5' | CGA GAT GAT AGT TTG CCC TC | (SEQ ID NO:32) |
| 161CR2 | 5' | AG CTA CTT CAC AGA TTG GGG AAA G | (SEQ ID NO:33) |

SM8D/C260   Size: 150 bp

| | | | |
|---|---|---|---|
| SM8D | 5' | CTC ATC TAG TCT CTG CTT CC | (SEQ ID NO:34) |
| 541C260 | 5' | TGG ATA TGG AAA TAG AGA GGG AGC | (SEQ ID NO:35) |

EXON4  SM3CA/C460   Size: 150 bp

| | | | |
|---|---|---|---|
| SM3CA | 5' | CAC CCT TAT AAC AAA AAC CTG C | (SEQ ID NO:36) |
| 541C460 | 5' | GAG AAA GGA GTT CCA TGG AGC AG | (SEQ ID NO:37) |

SM3CB/C380   Size: 180 bp

| | | | |
|---|---|---|---|
| SM3CB | 5' | GAG AGG TTA AAT GTC CCG AC | (SEQ ID NO:38) |
| 541C380 | 5' | GTG AGA ACT CCA GGT CTC CTG G | (SEQ ID NO:39) |

EXON5  EX55/C590   Size: 254 bp

| | | | |
|---|---|---|---|
| EX55 | 5' | TGA GTC TGT TTG ACT TCA GG | (SEQ ID NO:40) |
| 541C590 | 5' | GAA GGA AAT GGA GGC AGC CAG C | (SEQ ID NO:41) |

EX53/C550   Size: 168 bp

| | | | |
|---|---|---|---|
| EX53 | 5' | TTT CTA CCC ATT AGA ATC TGG | (SEQ ID NO:42) |
| 541C550 | 5' | CCC CAC TTA CTA TCA TGC TGG CTG | (SEQ ID NO:43) |

EXON6  164C25/C849   Size: 143 bp

| | | | |
|---|---|---|---|
| 164C25 | 5' | CCA GAC TTT ACT TTT TGT TTA CTG | (SEQ ID NO:44) |
| 541C849 | 5' | ATA GCC ACT CAT GTA CCA TGA | (SEQ ID NO:45) |

EX63/C618   Size: 248 bp

| | | | |
|---|---|---|---|
| EX63 | 5' | AAG AGT AAT TTA AGC CTC AGA CAG | (SEQ ID NO:46) |
| 541C618 | 5' | CTC CCA TAT GTC CAG ATT CTC TTG  3' | (SEQ ID NO:47) |

EXON7  R111/C770   Size: 200 bp

| | | | |
|---|---|---|---|
| R111 | 5' | AGA CTA TCA ACT TAA TTT CTG ATC A | (SEQ ID NO:48) |
| 541C770 | 5' | TAA GGA ATG TGA GCA CCT TCC TTC | (SEQ ID NO:49) |

R111/C261   Size: 244 bp

| | | | |
|---|---|---|---|
| R111 | 5' | AGA CTA TCA ACT TAA TTT CTG ATC A | (SEQ ID NO:50) |
| 164C261 | 5' | GTA AGA TTC ACT TTC ATA ATG CTG | (SEQ ID NO:51) |

INTRON7 164C45/164C265 Size: 220 bp

| | | | |
|---|---|---|---|
| 164C45 | 5' | CTT TAT GGT TTG TGG AAA ACA  3' | (SEQ ID NO:52) |
| 164C265 | 5' | GGC ATC ATA TCC TAA AGC TC | (SEQ ID NO:53) |

EXON8  C960/C1120   Size: 186 bp

| | | | |
|---|---|---|---|
| 541C960 | 5' | GTA ATA ACC AAA TGC AAT GTG AA | (SEQ ID NO:54) |

```
541C1120      5'   CTA CAA CAC CCT TCT CAC AG          (SEQ ID NO:55)

164C140/C920

164C140       5'   GGT GTC CAC AGA GGA CAT GG          (SEQ ID NO:56)

541C920       5'   AAG AGT TAA CCC ATT CCA GCT TCC     (SEQ ID NO:57)
```

The invention also concerns antisense DNA or RNA, capable of hybridizing with the C-BCD541 gene and particularly to the intron sequences, especially with the fragment of the introns which differ from the corresponding part in the T-BCD541 gene.

The invention also relates to a protein comprising the amino acid sequence of FIG. 1, or to a protein having the amino acid sequence of FIG. 8.

The protein relating to the sequence of FIG. 1 can be used in a composition for the treatment of motor neuron diseases, via oral, intra-muscular, intravenous administration, or via administration in the spinal cord fluid.

The invention further provides a kit for the in vitro diagnosis of motor neuron diseases, comprising:

a set of primers as described above;

reagents for an amplification reaction; and a probe for the detection of the amplified product.

According to another embodiment of the invention, a kit for the detection of the motor neuron diseases containing a hybridization probe as described above is provided.

Oligonucleotide probes corresponding to the divergences between he genes can be used.

The diagnosis can be especially directed to SMA motor neuron pathology.

The invention also concerns cloning or expression vectors comprising a nucleotide sequence as defined above. Such vectors can be, for example, plasmids, cosmids phages, YAC, pYAC, and the like. Preferably, such a vector has a motor neuron tropism. Especially for the purpose of defining means for gene therapy, it can be chosen among poliovirus vector, herpes virus, adenovirus, retrovirus vectors, synthetic vectors and the like.

Within the scope of the invention are contemplated further recombinant sequences. The invention also concerns recombinant host cells, i.e., yeasts, CHO cells, baculovirus, bone marrow cells, *E. coli,* fibroblasts-epithelial cells, transformed by the above recombinant sequences.

The invention also relates to a method for detecting motor neuron disorders including spinal muscular atrophy, amyotrophoc lateral sclerosis and primary lateral sclerosis, said method comprising the steps of:

(a) extracting DNA from a patient sample;

(b) amplifying said DNA with primers as described above;

(c) subjecting said amplified DNA to SCCP;

(d) autoradiographing the gels; and (e) detecting the presence or absence of the motor neuron disorder.

Steps (c) and (d) can be replaced by a step of digestion with BsrI enzyme or with any other enzyme capable of recognizing specifically the divergence of the genes or mismatches in genes, or by sequencing.

The invention also relates to a method for detecting spinal muscular atrophy, said method comprising the steps of:

(a) extracting DNA from a patient sample;

(b) hybridizing said DNA with a DNA probe comprising all or part of the cDNA sequence of FIG. 3 or of FIG. 2 under stringent conditions; and (c) detecting the hybrids possible formed.

The invention also relates to a method for detecting arthrogryposis multiplex congenita, said method comprising the steps of:

(a) extracting DNA from a patient sample;

(b) amplifying said DNA via PCR using unlabeled primers from exon 7 and exon 8 of the SMN gene;

(c) subjecting said amplified DNA to SCCP;

(d) autoradiographing the gels; and (e) detecting the presence or absence of arthrogryposis multiplex congenita.

Yet another method to detect arthrogryposis multiplex congenita concerns dinucleotide Repeat Polymorphism Analysis using genotyping markers C272 and C212 after PCR amplification.

The present invention further concerns polyclonal antiserum or monoclonal antibodies directed to the protein of FIG. 1 (SEQ ID NO: 9), the protein of FIG. 8 (SEQ ID NO: 19) or the protein of FIG. 12 (SEQ ID NO: 20).

Yet another aspect of the present invention is directed to the use of the entire or partial nucleotide sequence of SMN as a probe to detect SMA as well as to identify and clone genes related to SMN gene motor neuron in animals or organisms.

Yet another aspect of the present invention is the use of the SMA protein to produce polyclonal and monoclonal antibodies, which antibodies may be used to detect and diagnose SMA.

In another aspect, polyclonal rabbit antiserum were generated against synthetic peptides corresponding to the amino acid sequence of FIGS. 1, 8 and 12, including the amino acid terminus and the carboxy terminus.

Accordingly, in one of its process aspects, the present invention relates to the detection of SMA in patients having SMA or related motor neuron disorders such as AMC, ALS and PLS.

Yet another aspect of the present invention is to administer the SMN gene part thereof, cDNA or oligonucleotides to patients who are either lacking the gene or have a genetically defective gene as such or after incorporation into engineered viruses or vectors.

These and other aspects of the present invention will be discussed in detail below in the preferred embodiments of the present invention.

BRIEF DESCRIPTION OF THE DRAWINGS

FIG. 1 (SEQ ID NO: 9) is the amino acid sequence of the SMN coding region of the clone T-BCD541.

FIG. 2A (SEQ ID NO: 10) is the nucleotide sequence of the SMN coding region as well as the 5' and 3' flanking regions of clone C-BCD541; the coding region is underlined.

FIG. 2B (SEQ ID NO: 11) contains the sequence starting from intron 6 up to exon 8 of the C-BCD541 gene. The underlined sequences are those of exons 7 and 8. Sequences of introns 6 and 7 can be chosen as oligonucleotides to amplify the cDNA region allowing the distinction, within exon 7, between the T-BCD541 gene and the C-BCD541 gene. The position of the divergent nucleotide between the T-BCD541 and C-BCD541 cDNA are in italics.

FIG. 3A (SEQ ID NO: 12) is the nucleotide sequence of the SMN coding region as well as the 5' and 3' flanking regions of clone T-BCD541. The coding sequences are underlined. The numbers of the exons are indicated on the sequence. Asteriks indicate the beginning of each exon. The nucleotides which are indicated in italics are those which differ between the C-BCD541 and the T-BCD541 genes.

FIG. 3B (SEQ ID NO: 13) represents the sequence from intron 6 up to the end of exon 8 of the T-BCD541 gene. The sequence of exons 7 and 8 is underlined.

FIG. 4 is the nucleotide sequences of the markers C212 (SEQ ID NO: 14), C272 (SEQ ID NO: 15), C171 (SEQ ID NO: 18), AFM157xd10 (SEQ ID NO: 16), and C161 (SEQ ID NO: 17).

FIG. 5 represents various probes utilized in the present invention revealing several loci that the probes hybridized to.

FIG. 6 represents the telomeric element containing the survival SMN gene.

FIG. 8 (SEQ ID NO: 19) represents the amino acid sequence of the truncated SMN protein.

FIG. 10 (SEQ ID NO: 21) represents the nucleotide sequence and amino acid sequence of the entire human SMN gene including the introns and exons. Translated nucleotide sequences are in upper case, with the corresponding amino acids shown below that. The polyadenylation signal is in bold face. Arrowheads indicate the position of the single base differences between SMN and C-BCD541 genes in introns 6 and 7 and exons 7 and 8. Italic letters indicate the position of the oligonucleotides chosen for the detection of divergences in intron 7. (*) indicates the position of the stop codon.

FIG. 11 (SEQ ID NO: 22) represents the nucleotide sequence upstream of the coding region of the human SMN gene and illustrates the presence of putative binding sites for the transcription factors of AP-2, GH-CSE2, DTF-1, E4FI, HINF-A, H4TF-1, β-IFN and SpI. Bold letters indicate the dinucleotide repeat (CA) corresponding to the C272 markers.

FIG. 12 (SEQ ID NO: 20) represents the nucleotide and amino acid sequences of Mouse SMN cDNA. (*) indicates the position of the stop codon.

FIG. 13 represents a comparative analysis of the amino acid sequence of human SMN (above) and mouse SMN (below).

DETAILED DESCRIPTION OF THE PREFERRED EMBODIMENTS OF THE INVENTION

Figure 5:
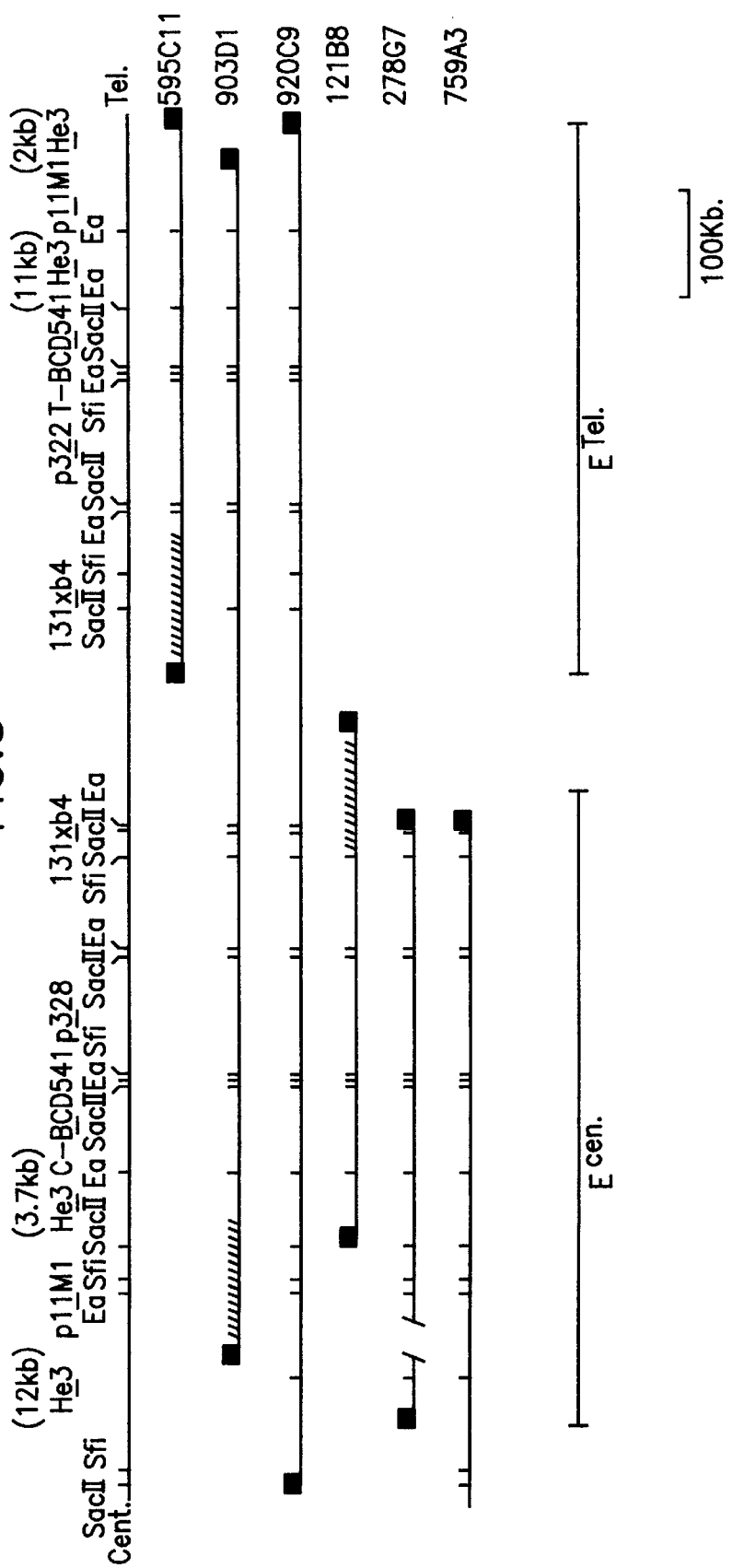
Figure 7:
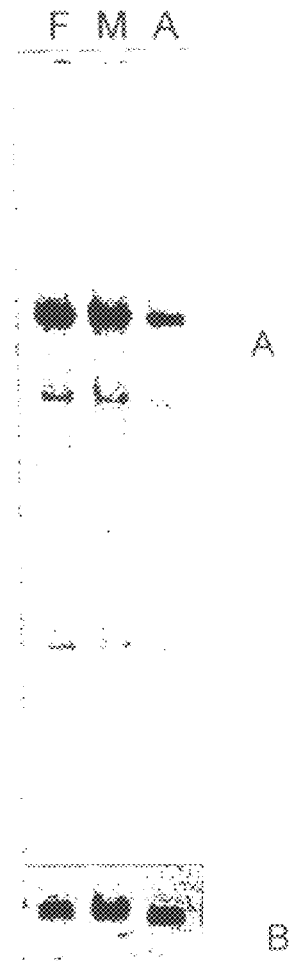
FIG. 7 represents the marked decrease of gene dosage with probe 132SEII, mapping close to this.

As used herein, the term "contig" means overlapping nucleotide sequences.

Previous studies by means of linkagee analysis have shown that all three forms of spinal muscular atrophy map to chromosome 5q11.2-q13.3. (L. M. Brzustowicz et al, Nature, 344, 540 (1990); J. Melki et al, Nature, 345, 823 (1990); J. Melki et al, Lancet, 336, 271 (1990). A yeast artificial chromosome (YAC) contig of the 5q13 region spanning the disease locus was constructed that showed the presence of low copy-repeats in this region. Allele segregation was analyzed at the closest genetic loci detected by markers derived from the YAC contig (C212, C272 and C161) in 201 SMA families. These markers revealed two loci (C212, C272) or three loci on the 5q13 region (C161). Inherited and de novo deletions were observed in 9 unrelated SMA patients. Moreover, deletions were strongly suggested in at least 18% of SMA type I patients by the observation of marked heterozygosity deficiency for the loci studied. These results indicated that deletion events are statistically associated with the sever form of SMA.

By studying all polymorphic DNA markers derived from the YAC contig, it was observed that the smallest rearrangement occured within a region bordered by loci detected by C161 and C212-C272 and entirely contained in a 1.2-Mb YAC clone 903D1. See, for example, French Patent Application No. 9406856 incorporated herein by reference.

The present invention characterized the small nested critical SMA region of about 140 Kb by a combination of genetic and physical mapping in SMA patients. This region suggested a precise location for the SMA gene and therefore, as limited region within which to search for candidate genes. The present invention identified a duplicated gene from the 5q13 region. One of them (the telomeric gene) is localized within the critical region. Moreover, this gene was lacking in 213 out of 230 (92.2%) or interrupted in 13 out of 230 (5.6%) SMA patients. In patients where the telomeric gene is not lacking or interrupted, deleterious mutations indicated that this telomeric gene, termed survival motor-neuron (SMN) gene, is the chromosome 5 SMA-determining gene.

The SMN gene was discovered using a complex system of restriction mapping, distinguishing the $E^{Tel}$ from the $E^{Cen}$ by Southern blot, and the determination of the differences between the $E^{Tel}$ in SMA patients by genetic and physical mapping. After confirming the location of the SMN gene, a phage contig spanning the critical region of the telomeric element was constructed to identify specific clones containing the SMN gene.

Analysis of the SMN gene in SMA patients compared with those of normal patients revealed either the SMN gene was either lacking or truncated in 98% of SMA patients or had combined mutations not present in normal control patients.

To identify a large inverted duplication and a complex genomic organisation of the 5q13 region, long-range restriction mapping using pulsed field gel electrophoresis (PFGE) of the YAC contig was performed.

YACs were ordered by comparing their haplotypes with that of the human donor at the polymorphic loci detected markers C212, C272, C171 C161 (FIG. 4 (SEQ ID NOS: 14–18).

The restriction enzymes SacII, BssHII, SfiI, EagI and XhoI were used to digest the YACs containing the telomeric loci detected by markers C212, C272, C171 and C161 (YAC clone 595C11), the centromeric loci detected by these markers (YAC clones 121B8, 759A3, 278G7) or both *YAC clones 903D1 and 920C9). Lambda phage libraries of YACs 595C11, 121B8 and 903D1 were constructed and subclones from phages containing markers C212 (p322), C272 (132SE11), C161(He3), AFM157xd10(131xb4) and CMS1 (p11M1) were used as probes for PFGE analysis. FIG. 5 shows that probes 132SE11, 11P1 and p322 revealed two loci, and probe He3 revealed 4 loci on the YAC contig, whereas probe 13xb4 revealed several loci on 5p and 5q13. The restriction map (FIG. 6) showed that the 5q13 region contained a large inverted duplication of an element (E) of at least 500 Kb, termed $E^{Tel}$ and $E^{Cen}$ for the telomeric and centromeric elements, respectively.

The PFGE analysis of SMA an control individuals revealed a high degree of variability of restriction fragments which hampered the distinghishment of $E^{Tel}$ from the $E^{Cen}$ and the recognition of abnormal restriction fragments in SMA patients.

In order to distinguish between the $E^{Tel}$ and the $E^{Cen}$, a Southern blot analysis was then performed. The Southern blot was performed by the methods described in Sambrook et al, supra.

More specifically, DNA from YAC clones, controls and SMA patients was digested with restriction enzymes SacI, KpnI, MspI, PstI, PvuII, EcrRI, HindIII, BglII and XbaI for Southern blotting and hybridized with clones 132SE11, 11p1, He3, 131xb4 and p322 as probes. None of the probes except one (He3) detected a difference between the two duplicated elements. Three HindIII restriction fragments of 12, 11 and 3.7 Kb were detected by probe He3. A 12 Kb HindIII restriction fragment was detected in YAC clones 754H5 and 759A3, indicating that this fragment corresponded to the most centromeric locus in the $E^{Cen}$. Conversely, a 11 Kb HindIII fragment was detected in YACs clones 595C11, 903D1 and 920C9 indicating that this fragment corresponded to a single locus on the $E^{Tel}$. Finally, a 3.7 Kb HindIII fragment was noted in non-overlapping YACs containing either $E^{Tel}$ or $E^{Con}$, indicating that this fragment corresponded to two different loci. Similar results were obtained with SacI and KpnI. The three restriction fragments detected by He3 were observed on the monochromosomal hybrid HHW105 (Carlock, L. R. et al, *Am. J. of Human Genet.*, 1985, Vol 37, p. 839) and in 30 unrelated, healthy individuals, confirming that these fragments were not due to polymorphisms. The Southern analysis results allowed one to distinguish $E^{Tel}$ from the $E^{Cen}$ in both controls and SMA patients.

Thus, once the $E^{Tel}$ from the $E^{Cen}$ was distinguished, it was necessary to determine the difference between the $E^{Tel}$ in SMA patients and those of the normal control. This was done by using genetic and physical mapping. This genetic and physical mapping identified genomic rearrangements in the telomeric element of $E^{Tel}$ of SMA patients.

It was previously shown that 9 out of 201 (9/201) SMA patients displayed large-scale deletions encompassing either one or the two loci detected by markers C212 and C272 on one mutant chromosome (J. Melki et al, *Science,* 264, 1474 (1994)). On the other hand, 22 out of 30 (22/30) patients born to consanguineous parents including 13 out of 14 (13/14) type I and 9 out of 10 (9/10) type III SMA, were homozygous by descent for the most closely flanking polymorphic markers.

The genomic DNA of the 9 patients harboring large scale deletions and the 22 consanguineous patients displaying homozygosity by descent were digested with HindIII for Southern blotting and hybridized with probe He3. The 11 Kb fragment revealed by probe He3 was absent in 12 out of 13 (12/13) consanguineous type I patients. In 2 out of 12 (2/12), the deletion also involved the 3.7 Kb fragment. By contrast, the 11 Kb fragment was absent in 1 out of 8 (1/8) consanguineous type III patients only. Consistently, the 11 Kb HindIII fragment was absent in 4 out of 9 (4/9) patients harboring large scale deletions on one mutant chromosome. Of particular interest was the absence of the 11 Kb fragment in the patient harboring a deletion of one of the two loci detected by markers C212 and C272.

When analyzed together, these observations provided evidence for genomic rearrangements of $E^{Tel}$ in SMA patients and supported the location of the SMA gene centromeric to the locus revealed by the 11 Kb HindIII fragment, since all consanguineous type III patients but one were not deleted for this locus.

In order to characterize the centromeric boundary of the genomic rearrangement in the disease, the allele segregation at loci detected by marker C272 in consanguineous SMA patients was analyzed. All consanguineous SMA type I patients had one single PCR amplification product, compared with 0 out of 60 controls. This marked heterozygosity deficiency was due to deletion of one of the two loci detected by C272, as indicated by the marked decrease of gene dosage with probe 132SE11, mapping close to this marker. By constrast, 7 out of 9 (7/9) consanguineous type III SMA patients had two C272 amplification products inherited from both parents, indicating homozygosity at each locus detected by marker C272. Moreover, no gene dosage effect was observed with probe 132SE11 indicating the absence of deletion involving the locus detected by C272 in type III consanguineous patients.

Assuming that the same locus is involved in all three types of SMA, these results indicate that the disease causing gene is distal to the telomeric locus detected by C272.

These studies place the SMA gene within the telomeric element $E^{Tel}$, between the telomeric loci detected by markers C272 and He3 (11 kb HindIII fragment). Based on long-range restriction mapping using PGFE of the YAC contig, this critical region is entirely contained in a 140 kb SacII fragment of YAC clone 903D1 (or 150 Kb SacII fragment of YAC clone 920D9).

After confirming that the SMN gene was located on a 140 Kb SacII fragment a phage contig spanning the critical region of the telomeric element was constructed in order to identify and characterize the SMN gene.

Phage clones containing markers C212, C272, C171 and C161 were isolated from the λ phage libraries constructed from YAC clones 595C11 and 903D1 and used as a starting point for bidirectional walking. A phage contig (60 Kb) surrounding markers C212, C272 and C171 was constructed based on the restriction map of the phage clones (FIG. 6).

To identify genes in the contig, the following three strategies were used:

1) a search for interspecies conserved sequences was conducted;
2) exon trapping method was performed; and
3) direct cDNA selection was performed. The genomic probe 132SE11, derived from the phage containing the marker C272, gave positive hybridization signals with hamster DNA indicating the presence of interspecies-conserved sequences. The screening of a λgt10 human fetal brain cDNA library with probe 132SE11 resulted in the selection of 7 overlapping λ clones spanning 1.6 kbp. Sequence analysis of the clones revealed a 882 bp open-reading frame (ORF) and a 580 bp non-coding region. A 1.5 kbp clone (BCD541) contained the entire coding sequence and most of the 3' non-coding region. The 3' end of the cDNA along with its poly(A)+ tail was obtained by PCR-amplification of a lymphoblastoid cell line cDNA library.

Two cDNA clones lacked nucleotides 661 to 755, suggesting that an alternative splicing might have occured. Northern blot analysis of poly(A)+ RNA from various tissues including heart, brain, liver, muscle, lung, kidney and pancreas, revealed the presence of a widely expressed 1.7 kb transcript. The ORF encodes a putative protein of 294 amino acids with a predicted molecular weight of approximately 32 Kd.

A homology search using the FASTA and BLAST networks failed to detect any homology at either the nucleotide or the amino acid level.

To further distinguish whether there was any duplication of the BCD541 gene in the 5q13 region, BCD541 cDNA was used as a probe for Southern blot and PFGE analysis of YAC clones spanning the disease locus.

Specific hybridization with non-overlapping YACs containing either the $E_{Cen}$ only (YAC clones 759A3, 121B8 and 278G7), or containing the $E^{Tel}$ only (YAC clone 595C11) provided evidence for duplication of the BCD541 gene. Each gene encompassed approximately 20 kb and displayed an identical restriction pattern. Evidence for head to head orientation of the two genes was derived from the location of the SacII and EagI restriction sites of the non-overlapping YAC clones containing either $E^{Cen}$ or $E^{Tel}$, following hybridization experiments with probes BCD541 and p322 which flank the SacII and EagI sites of each element.

In order to look for divergences in the two copies of the BCD541 gene, the organization of the telomeric gene was characterized and compared to that of the centromeric counterpart. Genomic sequence analysis revealed that the telomeric BCD541 gene is composed of 8 exons (FIG. 3). However, it is now known that the previously known exon 2 is composed of 2 exons separated by an additional intron as set forth in FIG. 10, therefore the SMN gene is composed of 9 exons.

Starting from either the centromeric or telomeric gene loci (in YAC clones 121B8 and 595C11, respectively), PCR-amplification and sequence of each exon and their flanking regions revealed five discrepancies between the centromeric and the telomeric BCD541 genes. The first one is a conservative substitution in exon 7 (condon 280) specific for the telomeric (TTC) or the centromeric BCD541 gene (TTT). The second one, located in the 3' non-coding region (exon 8 nucleotide n° 1155) is specific for the telomeric (TGG) or the centromeric BCD541 gene (TGA). Three other single base substitutions were observed in the sixth and seventh introns.

The observation of both versions of each exon (exon 7 and 8) on either YAC clones containing both gene loci (YAC clone 920C9) or the monochromosomal hybrid HIIW105 demonstrated that these substitutions are neither allelic nor due to polymorphisms. Band shifts on SSCP analysis of amplified exons 7 and 8 allowed an easy distinction of the telomeric (T-BCD541) and centromeric genes (C-BCD541) in both controls and SMA patients. All the unrelated healthy controls tested (n=75) harbored the T-BCD541 gene as determined by SSCP analysis of exons 7 and 8 (100%). Most of them (89.3%) also harbored the C-BCD541 gene but 8 out of 75 (8/75) (10.7%) lacked the C-BCD541.

A total of 230 SMA patients were tested for single base substitutions detected in exons 7 and 8 by SSCP method after PCR-amplification of genomic DNA. Among them, 103 belonged to type I, 91 to type II, and 36 to type III. Interestingly, 213 out of 230 SMA patients (92.6%) lacked the T-BCD541 gene on both mutant chromosomes compared with 0 out of 75 controls (0%). Moreover, 13 out of 230 SMA patients (5.6%) lacked the T-BCD541 gene for exon 7 on both mutant chromosomes but retained the T-BCD541 gene for exon 8 compared with 0 out of 75 controls (0%). Finally, only 4 out of 230 SMA patients (1.7%) harbored the T-BCD541 gene as determined by SSCP analysis of exons 7 and 8.

These results show that the T-BCD541 gene is either lacking or truncated in 98% of SMA patients. In addition, these data support the view that the disease gene is located between the telomeric locus detected by C272 and exon 8 of the T-BCD541 gene. Therefore, according to the overlapping restriction map of the phage contig, the critical region is entirely contained in 20 kb, suggesting that the telomeric T-BCD541 gene is the chromosome 5 SMA-determining gene.

In order to demonstrate that the T-BCD541 gene is responsible for SMA, point mutations in the 4 SMA patients in whom no rearrangement of the T-BCD541 gene had been observed were searched. Direct sequencing of PCR amplification products of each exon with their flanking regions was performed in the four patients.

A 7 bp deletion in the 3' splice acceptor site of intron 6 (polypyrimidine tract) was found in patient SA. Sequence analysis of exon 7 flanking the deleted intron, recognized the sequence specific for the T-BCD541 gene. Moreover, the non-delected PCR-product corresponding to the same region, harbored the sequence specific for the T-BCD541 suggesting that the other mutant allele lacked the T-BCD541 gene.

In patient BI, a 4 bp deletion in the 5' consensus splice donor site of intro 7 was found. This deletion occured on the T-BCD541 gene as determined by sequence analysis of the flanking exon 7.

In patient HU, a point mutation in codon 272 (TAT→TGT) was found. This mutation changed a Tyrosine to Cysteine. The patient was heterozygous for the mutation, presumably carrying a different SMA mutation on the other allele. All three mutations observed in patients SA, HU and BI were not detected in 100 normal chromosomes ruling out rare polymorphisms.

A different splicing of exon 7 distinguished the C-BCD541 from the T-BCD541 gene using reverse transcription-based PCR. Eleven SMA patients were selected for the analysis of their transcipts by Northern blot or reverse transciption-based PCR amplification. Eight of them belonged to type I, 1 to type II and 2 to type III. SSCP analysis of genomic DNA showed an absence of T-BCD541 gene in 10 patients and one patient (SA) had C-BCD541 and T-BCD541 genes for both exons 7 and 8. Six unrelated controls who harbored both C-BCD541 and T-BCD541 genes and 2 controls with only T-BCD541 gene were included in the present study.

The expression of this gene in lymphoblasts made it possible to analyze the BCD541 transcripts in cell lines derived from controls and SMA patients. Northern blot analysis of RNA from lymphoblastoid cell lines showed the presence of a 1.7 kb mRNA in all samples. None of the SMA patients showed a transcript of altered size. It was observed that a reduced level of transcripts was obtained when compared to the expression of the β-actine gene in 3 out of 4 type I SMA patients. Normal mRNA level were found for the other SMA probands.

Since the Northern blot analysis revealed the presence of a transcript in SMA patient who had the C-BCD541 gene only for both exons 7 and 8 as determined by SSCP analysis, these results indicated that both C-BCD541 and T-BCD541 genes were expressed. To prove whether both BCD541 genes were expressed, RT-based PCR amplification of RNA isolated from the lymphoblastoid cell lines from controls and SMA patients was used. Direct sequencing of PCR products flanking exons 7 and 8 revealed that patients who had C-BCD541 only displayed the sequence specific for the C-BCD541 gene. Controls who had both T-BCD541 and C-BCD541 genes, had two types of transcipts corresponding to both BCD541 genes. These results confirmed that both genes were expressed. In addition, 2 alternative splicings involving exon 5 or exon 7 that results in different transcripts were observed. The alternative splicing of exon 5 confirmed previous sequence data on the cDNA clones.

The analysis of the RT-PCR amplification products encompassing exons 6 to 8 showed that the spliced transcript keeping exon 7, was present in controls who had both C-BCD541 and T-BCD541 genes or controls who had the T-BCD541 gene only. Conversely, the alternative spliced transcript lacking exon 7 was observed in controls who had both genes, but not in controls who had the T-BCD541 gene only. These results indicated that the alternative spliced transcript lacking exon 7 was derived from the C-BCD541 gene only.

The transcript analysis of patient SA harboring a 7 bp deletion of the 3' splice acceptor site of intron 6 of the T-BCD541 gene revealed the presence of both spliced transcript keeping exon 7 and alternate spliced transcript lacking exon 7. Moreover, the sequence analysis of amplification products from the spliced transcript keeping exon 7, showed a sequence specific for the C-BCD541 gene (FIG. 2). These results demonstrated that the 7 bp deletion of intron 6 observed in patient SA was deleterious for the correct splicing of exon 7 of T-BCD541 gene only. In addition, because a differential splicing of exon 7 allowed one to distinguish the 2 BCD541 genes, this difference was analyzed among controls and SMA patients including patient SA. In controls, the amount of alternated spliced transcript lacking exon 7 was less abundant than that of spliced product keeping exon 7. Conversely, in SMA patients, the amount of alternated spliced transcript lacking exon 7 was equal or more abundant than that of spliced product keeping exon 7.

These results provide evidence for a difference between controls and SMA patients at the transcription level of these genes. The alternative spliced transcript lacking exon 7 resulted in a shorter ORF with a different C-terminus protein that might have effects on the protein function.

To further characterize the entire structure and organization of the human SMN gene, three genomic clones were isolated from a FIX II phage library derived from YAC clone 595C11 and screened with the full-length BCD541 cDNA (FIG. 2A) as a probe. After selecting several clones that hybridized to the probe, restriction mapping and Southern blot analysis indicated that phages L-132, L-5 and L-13 spanned the entire SMN gene.

These three phage clones were further subjected to sequencing using the Maxam-Gilbert or Sanger et al methods of sequencing disclosed in Sambrook et al supra.

The nucleotide and amino acid sequence of the entire SMN gene including exons and introns is set forth in FIG. 10. The human gene is approximately 20 kb in length and consists of nine (9) exons interrupted by 8 introns as shown in FIG. 10. The human SMN gene has a molecular weight of approximately 32 kDA.

Figure 9:
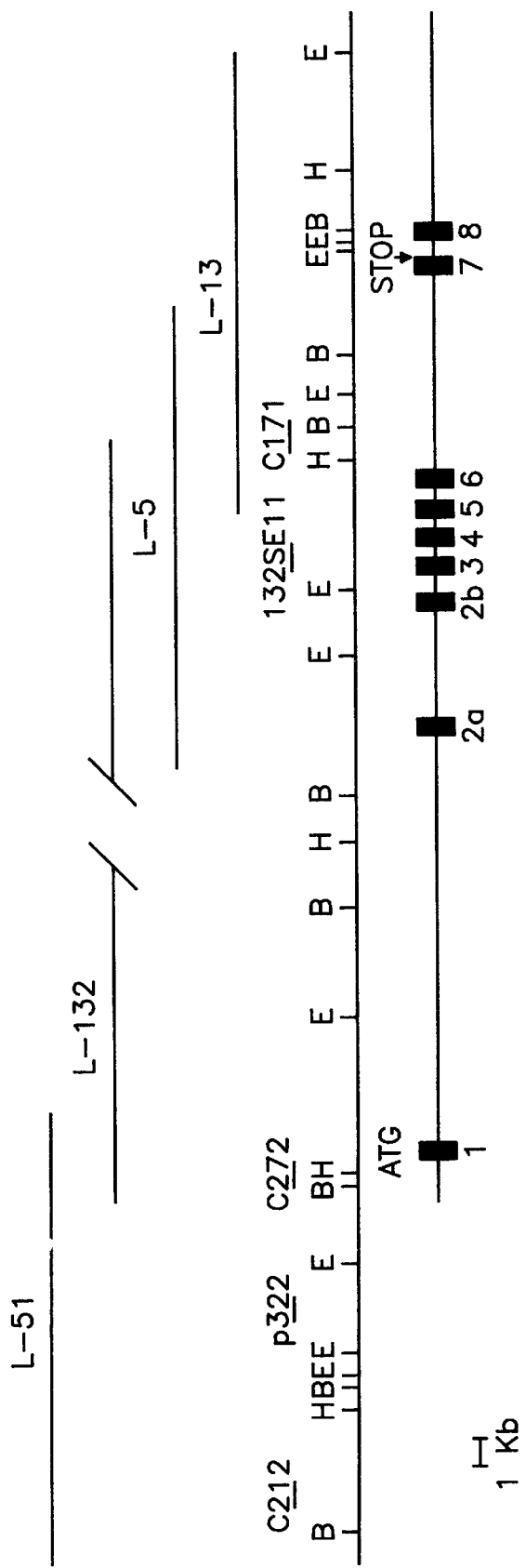
FIG. 9 is a schematic representation of the genomic structure of the human SMN gene. The designations and positions of genomic clones are shown above the figure. L-132, L-5, and L-13 depict the genomic clones spanning the entire SMN gene, while L-51 spans part of exon 1. Micro satellites and DNA markers are indicated above the genomic map. B, H, and E mean BgIII, HindIII and EcoRI, respectively. C212, p322, C272, 132SEII and C171 represent various markers. 1, 2a, 2b, 3, 4, 5, 6, 7, and 8 represent exons of the SMN and C-BCD541 genes. The entire sequence of L-132 is obtained by PCR amplification from exon 1 to exon 2A.

Although it was thought that only one exon 2 was present in the SMN gene (see, Lefebvre et al, *Cell,* 80:155–165 (1995)), the sequencing data proved otherwise and the previously mentioned exon 2 in Lefebvre et al supra is in fact composed of 2 exons separated by an additional intron, as illustrated in FIGS. 9 and 10. To avoid confusion in the renumbering of exons, the 2 exons in exon 2 are now referred to as exon 2a and exon 2b.

All exon-intron bounderies displayed the consensus sequence found in other human genes and a polyadenylation consensus site is localized 550 bp downstream from the stop codon (FIG. 10).

Figure 15:
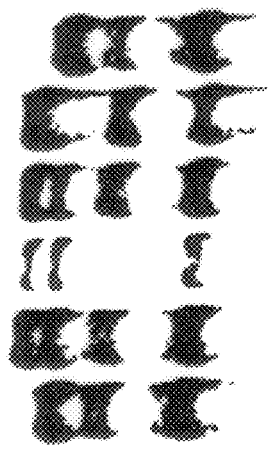
FIG. 15 illustrates the band shifts on single strand confirmation polymorphism (SSCP) analysis of the PCR amplified intron 7 and permitted indetification of SMN (closed arrowheads) and its centromeric counterpart C-BCD541 (open arrowheads).

Starting from either YAC clones 121B8 or 595C11 (which contain the C-BCD541 and SMN genes respectively, (see, Lefebvre et al, supra) PCR amplification and sequence analysis of the introns showed three differences between SMN and C-BCD541 in addition to those previously described (by Lefebvre et al, supra). These included a base charge in intro 6 (−45 bp/exon 7, atgt, telomeric, atat, centromeric) and two changes in intron 7 (+100 bp/exon 7, ttaa, telomeric; ttag, centromeric and at position +214 bp/exon 7, ttat, telomeric; ttgt, centromeric, FIG. 10). The presence of both versions in a YAC clone containing both genes (YAC 920C9), and in the control population demonstrated that these substitutions are locus-specific rather than due to polymorphism. Band shifts on single strand conformation polymorphism (SSCP) analysis of the PCR amplified intron 7 allowed SMN and its centromeric counterpart (C-BCD541) to be readily distinguished (see, FIG. 15).

In order to identify sequences potentially important for promoter function, the organization of the region surrounding exon 1 of the SMN and C-BCD541 genes was characterized. Based on restriction mapping, Southern blot hybridization and PCR amplification, exon 1 and the C272 marker (D5F150S1, D5F150S2) were located in the same BgIII-EcoRI restriction fragment of L-132 phage (FIG. 9). PCR amplification using the C272f primer and a reverse primer chosen in exon 1 was performed and the amplified product was directly sequenced. Sequence analysis showed that the (CA) repeat corresponding to the C272 marker are located 463 bp upstream from the putative ATG translation start site (FIG. 11). Comparative sequence analyses showed no discrepancy between the 5' ends of the SMN gene and its centromeric counterpart (C-BCD541). In addition, sequence analysis showed the presence of putative binding sites for the following transcription factors: AP-2, GH-CSE2, DTF-1, E4F1, HiNF-A, H4TF-1, β-IFN, Sp1 (FIG. 11; Faisst et al, *Nucleic Acids Res.,* 20:3–26 (1992)).

Besides isolating and characterizing the human SMN gene, the mouse homologue of the SMN gene was also cloned. Cross-species conservation of human SMN gene with rodents has been shown in Lefebvre et al, supra and served to isolate the mouse SMN gene. Screening of a mouse fetal cDNA library using human SMN cDNA as a probe allowed the isolation of 2 overlapping mouse cDNA clones. Sequences analysis of the clones revealed an 864 bp open-reading frame (ORF) (FIG. 12). The ORF encodes a putative protein of 288 amino acids (FIG. 12) with an homology of 83% with human SMN amino acid sequence (FIG. 13).

Either the isolated human or the mouse SMN, the gene can be inserted into various plasmids such as pUC18, pBr322, pUC100, λgHI, λ18–23, λZAP, λORF8, and the like. The methods for inserting genes into different plasmid vectors are described by Sambrook et al supra. Various microorganisms can be used to transform the vector to produce the SMN gene. For example, host microorganisms include, but are not limited to, yeast, CHO cells, *E. coli, Bacillus subtilis* and the like.

Once recombinantly produced, the human SMN protein or the mouse SMN protein can be further purified from the host culture by methods known in the art.

Besides recombinantly producing the SMN protein, the present invention also relates to the production of polyclonal and monoclonal antibodies. These methods are known in the art as evidenced by Sambrook et al supra. The monoclonal antibody can be obtained by the procedure of Kohler and Milstein, *Nature,* 256:495 (1975); *Eur. J. Immunol.,* 6:511 (1976) or Harlow and Lane Antibodies, a Laboratory Manual, Cold Spring Harbor Laboratory, Cold Spring Harbor, New York (1988), and can be used, for example, in diagnosing SMA, as well as other motor neuron disorders.

Polyclonal rabbit antisera can also be generated against synthetic peptides corresponding to any part of the SMN amino acid sequence including the amino terminus and carboxy terminus. More specifically, the following peptides were synthesized based on the amino acid sequence set forth in FIG. 1:

```
N-terminal    G G V P E Q E D S V L F R R G T  (residues 9–25 of SEQ ID NO:9)    C-terminal S R S P G N K S D N I K P K      (residues 173–186 of SEQ ID NO:9)

F R Q N Q K E G R C S H S L N    (residues 200–294 of SEQ ID NO:9)
```

The synthetic peptide may be coupled to a carrier protein such as Keyhole limpet hemocyanin (KLH) through an amino- or carboxy-artificial cysteine residue that may be synthetically added to the desired sequence. The cysteine residue is used as a linker to couple the synthetic peptide to the carrier protein. The procedure utilized to couple synthetic peptides to KLH is described by Green et at, *Cell,* 28:477 (1982).

Approximately, 50–100 μg, preferably 100 μg of synthetic antigen is dissolved in buffer and emulsified with an equal volume of Freund's complete adjuvant. About 0.025 ml to 0.5 ml of emulsified antigen-adjuvant can be injected intramuscularly or intradermaly into a rabbit. Four to six weeks later, the rabbit is boosted and 20–40 ml of blood is drawn 7–10 days after each booster injection. The serum is then tested for the presence of antigen using RIA, ELISA or immunoprecipitation. The positive antibody fractions may then be purified, for example by absorption to protein A following the method of Goudswaald et al, *Scand. J. Immunol.,* 8:21 (1978).

More specifically, about 20 to 50 μg of antigen, prepared either by the recombinant techniques set forth above or synthetically made antigen is diluted in about 100 μl of buffer and emulsified with an equal amount of Freund's complete adjuvant. About 30–60, preferably 50 μl of the emulsified antigen-adjuvant is injected subcutaneously at four sites into mice. Four to six weeks later, the mice are boosted with an intraperitoneal injection of about 100 μl containing 5–10 μg of antigen solubilized in buffer. The mice are bled from the mediam tail vein 7–10 days after the boaster injection and the serum is tested for antibody using standard methods. Blood is then drawn every 3–4 days until the antibody titer drops.

Tissue, plasma, serum, cerebral spinal fluid and the like can be used to detect SMA disease using the above-described monoclonal or polyclonal antibodies via Western blot (1 or 2 dimensional) or ELISA. These methods are known in the art as described by Sambrook et al, supra.

A method for detecting SMA as well as in ALS, ACM, and PLS patients who possibly have these motor neuron disorders, is also encompassed by the present invention. This method involves extracting from a patient suspected of having SMA, DNA from a sample. This sample may include sera, plasma, cerebral spinal fluid and the like. After extracting the DNA by known methods in the art, primers that are derived from exons 7 and 8 of the SMN gene are used to amplify the DNA.

After amplification with the primer, the amplified product is subjected to SSCP (Single Strand Conformation Polymorphism).

The gels are then subjected to autoradiography to determine if SMA is present in the sample.

More specifically, it has recently been discovered that in twelve cases of arthrogryposis multiplex congenita (AMC) associated with SMA, 6 out of 12 patients lacked the SMN gene.

A total of twelve unrelated patients including eight males and four females of various geographic origins was selected for the study. The patients were chosen based on the criteria that these patients had:

(1) congenital joint contractures of at least two regions of the body (see, Stern, *JAMA*, 81:1507–1510 (1923));
(2) generalized muscle weakness with muscular atrophy and are flexia without extraocular involvement;
(3) electromyographic studies showed denervation and diminished motor action potential amplitude; and
(4) muscle biopsies consistent with denervation with no evidence of storage material or other structural abnormalities (see, Munsat, *Neuromuscular Disorders*, 1:81 (1991)).

The study consisted of Dinucleotide Repeat Polymorphism Analysis and SMN gene analysis (see, Examples) based on DNA extracted from peripheral blood leukocytes, lymphoblastoid cell lines or muscle tissue in all twelve patients.

The data from this study is summarized in Table 1 below.

The diagnosis was made at birth with an uniform phenotype characterized by a severe hypotonia, absence of movements except extraocular mobility and contractures of at least two joints. The number of affected joints and the severity of the postural defects varied from infant to infant, as set forth in Table 1. Decreased fetal movements were noted in 7 out of 12 (7/12) patients. Neonatal respiratory distress was observed in 9 out of 12 (9/12) patients and facial involvement associated with micrognathia was noted in 4 out of 12 (4/12) patients. Most of the cases, 8 out of 12 (8/12), died within the first month of life. Four infants are still alive. No family history was noted except in family 12 in which both the child and her father were affected suggesting an autosomal dominant form of AMC.

Figure 14A:
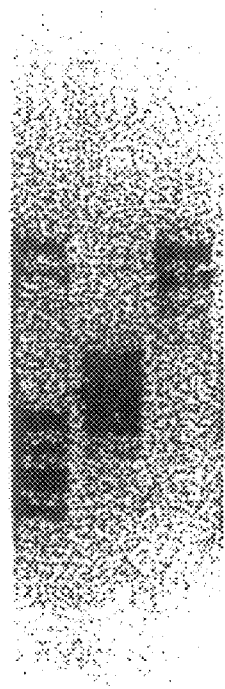
FIGS. 14A–C illustrates the genetic analysis of family 6. Lane A shows evidence of inherited maternal deletion seen with the microsatellite marker C272 as the proband inherited only allele from the father. Lanes B and C represent SSCP analysis of PCR-amplified exons 7 (lane B) and 8 (lane C) of SMN (closed arrowheads) and its centromeric copy (open arrowheads). "F" represents the father, "M" the mother, "A" the affected infant.
Figure 14B:
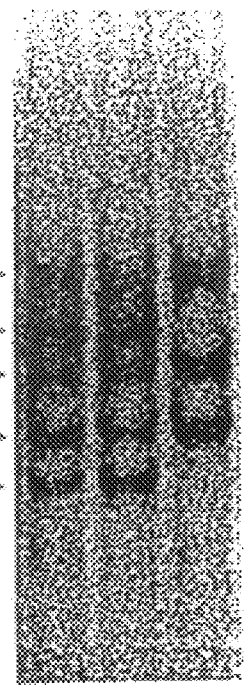
Figure 14C:
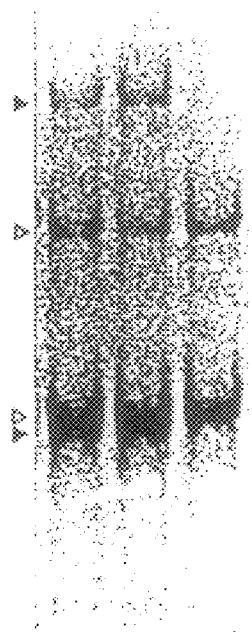

Table 1 shows that the SMN gene was lacking on both mutant chromosomes in 6 out of 12 (6/12) patients (cases 1–6). Among them, 3 out of 6 (3/6) patients had a large inherited deletion involving both loci detected by markers C212 and C272 on one parental allele, the other parental carrying only one locus instead of the expected two, as shown in FIG. 14.

Analysis of SMN exons did not reveal intragenic mutations in the patients whose SMN gene showed no deletions (cases 7–12). Genetic analysis showed that the disease gene in a family (case 9) was not linked to chromosome 5q13 as both the affected and healthy siblings carried the same 5q13 haplotype. These data strongly suggest that the patients whose SMN gene showed no deletions were not linked to the 5q13 SMA locus (cases 7–12).

Hithto, arthrogryposis was regarded as an exclusion criterion in SMA (see, Munsat, supra). But the observation of SMN gene deletion in 6 out of 12 (6/12) patients (50%) strongly indicates that arthrogryposis of neurogenic origin is related to SMA and that this subgroup and SMA are allelic disorders. Yet, AMC of neurogenic origin is a genetically heterogeneous condition since the disease gene was not linked to SMN locus in 6 out of 12 (6/12) patients. Exclusion of chromosome 5q has also been shown in one family with two AMC-SMA patients, as described by Lunt et al, *J. Med. Genet.*, 29:273 (Abstract) (1992).

Thus, by dinucleotide Repeat Polymorphism Analysis and SMN gene analysis, clinical diagnosis of AMC can be confirmed by the absence or interruption of the SMN gene. The present invention now provides methods to detect AMC either in live patients or in utero.

Yet another embodiment of the present invention is the detection of SMA using specific oligonucleotide probes based on the nucleotide sequence set forth in FIGS. 3, 10, or for the mouse SMA FIG. 12. If a patient totally is lacking in the SMN gene, no hybridization to the specific probe will occur. The hybridization conditions may vary depending upon the type of sample utilized. It is preferable to conduct such hybridization analysis under stringent conditions which are known in the art and defined in Sambrook et al supra. The oligonucleotide probes may be labeled in any manner such as with enzymes, radioactivity and the like. It is preferable to use radiolabeled probes.

In another embodiment of the present invention, the human SMN gene can be utilized in conjunction with a viral or non-viral vector for administration in vivo directly to the patients suffering from SMA or related motor neuron diseases or by administration in vitro in bone marrow cells, epithelial cells fibroplasts, followed by administration to the patient. See, for example Resenfeld et al, *Science* (1991) 252, pp. 431 to 434.

The present invention provides a method of detecting SMN gene defects or the total lack of the SMN gene in a fetus. Amniotic fluid taken from the pregnant woman is subjected to SSCP analysis according to the methods of the present invention.

In order to further illustrate the present invention and advantages thereof, the following specific examples are given, it being understood that the same are intended only as illustration and in nowise limitative.

EXAMPLES

Example 1

Construction of Phage Libraries From the 121B8, 595C11, and 903D1 YAC clone

Total yeast DNA from YAC clone 595C11 containing the telomeric loci detected by C212, C272 and C161, or YAC clone 12B8 containing the centromeric loci detected by the same markers or 903D1 YAC clone containing both loci was purified and partially digested with Sau3A. DNA in the size range of 12 to 23 kb was excised after 0.5% Seaplaque GTG agarose gel electrophoresis and precipitated with ethanol after β-agarase digestion. After partial fill-in of the Sau3A site, DNA was subcloned at the partially filled XhoI site of bacteriophage FIXIII (Stratagene). Clones of λ containing the microsatellite DNA markers C212 (L-51), C272 (L-51, L-132), C171 (L-5, L-13), C161 (595B1), 11M1 (L-11), AFM157xd10 (L-131) were digested either with EcoRI or HindIII or both and subcloned into pUC18 plasmid vectors. Subclones from phages containing markers C212(p322), C272(132SE11), C161(He3), AFM157xd10(131xb4) and CMS1(p11M1) were used as probes.

Example 2

Pulsed Field Gel Electrophoresis Analysis

High molecular weight DNA was isolated in agarose plugs from Epstein-Barr virus transformed lymphoblastoid cell lines established from controls and patients or from YAC clone as described. Plugs were rinsed twice for 30 min. each in 10–20 min vol. TE. The plugs were equilibrated for 30' at 4° C. with 0.3 ml of the appropriate restriction enzyme buffer containing 0.1 mg/ml BSA (Pharmacia). Excess buffer was then removed and the plugs were incubated at the appropriate temperature for 16 h with 40 U restriction enzyme per reaction. DNA was digested with the restriction enzymes BssHII, EagI, SfiI, SacI, KpnI, SacII, SpeI. Separation of DNA fragments was performed using a CHEF-III-DR PFGE apparatus (Biorad). Fragments from 50 to 1200 kb were separated by electrophoresis through 1% agarose Seakem, at 200 V for 24 h at 14° C. in 0.5×TBE running buffer using a 30' to 70' ramping pulse time. The separation of fragments from 5 to 100 kb was performed by electrophoresis at 200 V for 19 h at 14° C. in 0.5×TBE buffer using a 5' to 20' ramping pulse time. After treatment with 0.25N HCl for 20 min, pulsed field gels were blotted onto Hybond N+ Nylon membrane (Amersham) in 0.4N NaOH, 0.4M NaCl for 20 h. Probes were successively hybridized to the same filters to ensure accurate data Hybridizations were performed as described.

Example 3

YAC Library Screening

YAC libraries from CEPH were screened by PCR with microsatellites C212, C272, C171, CMS1, and C161. YAC geneotypes were established by electrophoresis of PCR products on denaturing polyacrylamide gels. YAC size was estimated by pulsed field gel electrophoresis.

Example 4

Southern Blot Analysis

DNA samples were extracted from either peripheral blood leukocytes or lymphoblastoid cell lines. DNA were digested with restriction enzymes EcoRI, HindIII, BgIII, XbaI, PvuII, XmnI, RsaI, PstI, BamHI, separated by electrophoresis on an 0.8% agarose gel for Southern blotting and hybridized with radioactively labeled probes.

Example 5

Dinucleotide Repeat Polymorphisms

Genotypic data were obtained for the C212(D5F149S1, -S2), C272(D5F150S1, -S2) and C161(D5F153S1, -S2) dinucleotide repeat. Amplification conditions were as follows: denaturation at 94° C., annealing at 55° C., and extension at 72° C., 1 min each for 30 cycles. The procedure used for detection of dinucleotide repeat polymorphisms has been described elsewhere.

Example 6 cDNA Clone and DNA Sequencing

Two million recombinants of a λgt10 human fetal brain library were plated according to the manufacturer (Clontech). Prehybridization and hybridization was carried out in 10% Dextran Sulphate Sodium, 1 M NaCl, 0.05 M Tris-HCl pH 7.5, 0.005 M EDTA and 1% SDS with 200 mg/ml sheared human placental DNA (Sigma) for 16 hours at 65° C. The filters were washed in 0.1×SSEP-0.1% SDS at 65° C. and autoradiographs were performed for 24 hours. The DNA of positive cDNA clones were purified, digested with EcoRI and subcloned in M13 bacteriophage. Single strand DNAs were sequenced using the DyeDeoxy™ Terminator Cycle Sequencing Kit protocol supplied by Applied Biosystems, Inc. and analyzed on a ABI model 373A DNA automated sequencer. To obtain the 3' end of the cDNA along with its poly(A)$^+$ tail, PCR-amplification of a lymphoblastoid cell line cDNA library was performed using specific primer complementary to the 3' end of the clones and primer specific to the vectors arms of the cDNA library as previously described (Fournier B., Saudubray, J. M., Benichou, B. et al, 1994, *J. Clin. Invest.* 94:526–531). Specific PCR-products were directly sequenced with both primers using the DyeDeoxy™ Terminator Cycle Sequencing Kit protocol supplied by Applied Biosystems, Inc. and analyzed on a ABI model 373A DNA automated sequencer.

Example 7

Isolation of RNA and Northern Blot Analysis mRNA from lymphoblast cell lines of controls and SMA patients were isolated with the QuickPrep mRNA purification kit (Pharmacia) according to the supplier's procedure. Total RNA was prepared following the single-step RNA isolation method described by Chomczynski and Sacchi (*Analytic Biochemistry*, 162:156–159 (1987)). The total RNA preparation was treated with RQ1-DNAse (Promage) to remove any contaminating genomic DNA. Northern blots were made from mRNA and total RNA by electrophoresis through 1.5% seakem agarose gel containing methyl mercuric hydroxide and transferred to positively charged membrane in 20×SSC and heated for 2 hours at 80° C. $^{32}$P-radiolabeled DNA probes were synthesized by a random priming method according to the manufacturer (Boehringer), and hybridized in a solution containing 5×SSEP, 1% SDS, 5×Denhardt's for 16 hours at 65° C. The membranes were washed to a final stringency of 0.1×SSEP, 0.1% SDS at 65° C. for 10 min. Autoradiography was at −80° C. with intensifying screens and Kodak XAR films for 2 to 10 days. The amount of mRNA was normalized with a b-actine cDNA probe. The autoradiographs were scanned at 600 nm in computerized densitometer (Hoeffer Scientific Instruments, San Francisco). A Northern blot with polyA+ RNA from several huma tissue was purchased from Clontech.

Example 8

Reverse Transcriptase-Based PCR Amplification and Sequencing

Each PCR amplification was carried out in a final volume of 20 ml on single-strand cDNAs synthesized from the random hexamers-primed reverse transciption (Promega). The PCR reactions included 2 picomoles of forward and reverse primers and 1 unit Taq polymerase in the reaction buffer recommended by Perkin Elmer/Cetus. Parameters for PCR amplification consisted in 1 min at 94° C., 1 min at 55° C. and 1 min at 72° C. for 30 cycles followed by a final extension period of 10 min at 72° C. Parameters for PCR amplification consisted in 1 min at 94° C., 1 min at 55° C. and 1 min at 72° C. for 30 cycles followed by a final extension period of 10 min at 72° C. The PCR products were cut from acrylamide gel and eluted in 100 ml of TE buffer. The diluted fragments were reamplified with the same primers prior direct sequencing. The PCR amplification products were cut from acrylamide gel and eluted in 100 ml of TE buffer. The diluted fragments were reamplified prior to direct sequencing with both primers using the DyeDeoxy™ Terminator Cycle Sequencing Kit protocol supplied by Applied Biosystems, Inc. and analyzed on a ABI model 373A DNA automated sequencer. Six sets of primers along the cDNA sequence were used to amplify DNA products for sequence analysis.

Example 9

Computer-Assisted Analysis

Sequence homology analysis with both nucleotide and protein sequences from 541C were performed using FASTA and BLAST through the CIT12 French network (Dessen, P., Fondrat, C., Velencien, C., Mugnoer, C., 1990, CABIOS; 6:355–356).

Example 10

SSCP Analysis

For single strand conformation polymorphism (SSCP) analysis, DNA from peripheral leukocytes (200 ng) was submitted to PCR amplification using unlabelled primers (20 μM) in 25 μl amplification mixture containing 200 μM dNTPs, 1 unit of Taq polymerase (Gibco-BRL) and 0.1 μl of a $^{32}$P dCTP (10 mCi/ml, NEN). Amplified DNA was mixed with an equal volume of formamide loaded dye (95% formamide, 20 mM EDTA, 0.05% bromophenol blue, 0.05% xylene cyanol). The samples (5 μl) were denatured for 10 mn at 95° C. and loaded onto a polyacrylamide gel (Hydroling MED, Bioprobe) and electrophoresed at 4° C. for 18 to 24 hours at 4W. Gels were transferred onto 3 MM Whatman paper, dried and autoradiographed with Kodak X-OMAT films for 24 hours. To amplify the DNA sequence containing the divergence of exon 7 oligonucleotides R111 (5' AGACTATCAACTTAATTTCTGATCA 3') (SEQ ID NO: 5) and 541C770 (5'TAAGGAATGTGAGCACCTTCCTTC 3') (SEQ ID NO: 6) were used. To amplify the DNA sequence containing the divergence of exon 8 oligonucleotides 541C960 (5' GTAATAACCAAATGCAATGTGAA 3') (SEQ ID NO: 7) and 541C1120 (5' CTACAACACCCTTCTCACAG 3') (SEQ ID NO: 8) were used.

Example 11

Cloning of the Human SMN Gene

Total yeast DNA from YAC clone 595C11 was purified via the method of Sambrook et al supra and partially digested with restriction enzyme Sau3A. DNA in the 12–23 kD size range was excised after 0.5% sea plague GTG agarose gel electrophoresis and precipitated with ethanol after β-agarose digestion. After partial fill-in of the Sau3A site, DNA was subcloned at the partially filled XhoI site of bacteriophage FIXII (Stratagene).

The full-length BCD541 cDNA was used as a probe to screen the FIXII phage library under conditions set forth in Sambrook et al, supra.

These phages, named M-132, L-5 and L-13 spanned the entire SMN gene as confirmed by restriction mapping using HindIII, EcoRI and BgIII (see, FIG. 9) and Southern blot analysis.

The phages were then sequenced as described in Example 8. Once the gene was sequenced, it was then cloned into a pUC18 vector and recombinantly reproduced in large quantities that were purified for further use.

Example 12

Cloning of the Mouse SMN Gene

A mouse fetal cDNA library was screened using the coding sequence of the human SMN cDNA as a probe according to Sambrook et al, supra.

Two overlapping mouse cDNA clones were found that had the entire sequence of mouse SMN, as revealed by sequencing methods described in Example 8 after being cloned into a pUC18 vector and M13 vectors.

Example 13

Transgenic Mouse

Transgenic mice containing multiple normal SMN genes OR SMN genes lacking exon 7 are produced by the methods according to Lee et al, *Neuron,* 13: 978–988 (1994). The transgenic animals are then tested and selected for the overexpression of the SMN gene or SMN gene lacking exon 7 via Southern, and/or Northern blots using the probes described in the present invention or by screening with antibodies described in the present invention in a Western blot.

Transgenic mice containing abnormal SMN gene are obtained by homologous recombination methods using mutated SMN genes as described by Kühn et al, *Science,* 269: 1427–1429 (1995) and Bradley, *Current Opinion in Biotechnology,* 2: 823–829 (1991). The transgenic animals are then tested and selected for the overexpression of the SMN gene via Southern, and/or Northern blots using the probes described in the present invention or by screening with antibodies described in the present invention in a Western blot selected for the abnormal SMN gene.

Example 14

Polyclonal Antibodies

100 μg of a synthetic antigen having sequence:

```
N-terminal    G G V P E Q E D S V L F R R G T  (residues 9-25 of SEQ ID NO:9)    C-terminal
``` was dissolved in buffer and emulsified with an equal volume of Freund's complete adjuvant. 0.5 ml of the emulsified synthetic antigen-adjuvant was injected intramuscularly into a rabbit. Five weeks later, the rabbit was boosted and 20–40 ml of blood was drawn 8 days after each injection. The serum was then tested for the presence of antigen using RIA.

Polyclonal antibodies were also prepared by the same methods using the following sunthetic antigens:

```
N-terminal    S R S P G N K S D N I K P K    (residues 173-186 of SEQ ID NO:9)    C-terminal
              F R Q N Q K E G R C S H S L N  (residues 280-299 of SEQ ID NO:9)
```

Example 15

Gene Therapy

Using the adenovirus construct described by Ragot et al, *Nature,* Vol. 361 (1993), the normal SMN gene was inserted therein and injected intramuscularly into a patient lacking this gene. The patient is monitored using SSCP analysis as described in Example 10 above.

While the invention has been described in terms of various preferred embodiments, the skilled artisan will appreciate that various modifications, substitutions, omissions and changes may be made without departing from the spine thereof. Accordingly, it is intended that the scope of the present invention be limited solely by the scope of the following claims, including equivalents thereof.

TABLE 1

| Case | 1 | 2 | 3 | 4 | 5 | 6 | 7 | 8 | 9 | 10 | 11 | 12* |
|---|---|---|---|---|---|---|---|---|---|---|---|---|
| Sex | m | f | m | m | m | m | m | m | m | f | f | f |
| Age of death | d8 | d6 | d1 | d25 | d11 | d13 | 4m | >3y | >3y | d20 | >9y | >16m |
| Fetal movements diminished | + | + | − | + | − | − | + | − | + | − | + | + |
| Hypotonia | + | + | + | + | + | + | + | + | + | + | + | + |
| Respiratory Involvement | + | + | + | + | + | + | + | − | + | + | − | − |
| Neurogenic (EMG) | ? | + | + | + | + | + | nd | + | + | + | + | + |
| Muscle Atrophy (MB) | + | + | + | + | + | + | + | + | + | + | + | + |
| Contractures | | | | | | | | | | | | |
| Hips | − | − | − | − | − | + | − | + | − | − | + | + |
| Knees | + | + | + | + | + | + | − | + | − | − | + | + |
| Ankle | + | − | − | + | − | − | − | + | + | + | + | + |
| Elbows | − | + | + | + | − | − | + | + | − | − | − | − |
| Wrists | − | − | + | − | + | + | + | + | − | + | − | − |
| Fingers | − | + | − | − | + | + | − | − | − | − | − | − |
| Associated Signs | facial micro − | Ao.Co. | − | − | − | − | fract. | − | facial micro − | facial micro − | facial micro − | − |
| C212/C272 markers | + | + | del | del | + | del | + | + | unlink | + | + | + |
| SMN gene | del | del | del | del | del | del | + | + | + | + | + | + |

Abbreviations: +, present; −, absent; Ao.Co, aortic coartation; Fract., bone fracture, Facil. microg, facial involvement with micrognathia; nd, not done. *Both the child and her father were affected.

---

We claim:

1. An isolated nucleic acid encoding a survival motor neuron (SMN) protein of SEQ ID NOS: 9 or 19.

2. An isolated nucleic acid comprising nucleotides 34 to 915 of SEQ ID NO: 12.

3. An isolated nucleic acid comprising nucleotides 34 to 915 of SEQ ID NO: 10.

4. An isolated nucleic acid comprising the mouse SMN cDNA sequence of SEQ ID NO: 20.

5. An isolated nucleic acid comprising a sequence fully complementary to the sequence of any one of claims 1, 2, 3 or 4.

6. A cloning or expression vector, wherein said vector comprises a sequence according to any one of claims 1, 2, 3 or 4.

7. The vector according to claim 6, wherein said vector comprises a poliovirus, an adenovirus, a retrovirus or a herpes virus.

8. An isolated host cell, wherein said host cell comprises a vector according to claim 6.

* * * * *

SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
       (A) LENGTH: 347 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
AATTTTTAAA TTTTTTGTAG AGACAGGGTC TCATTATGTT GCCCAGGGTG GTGTCAAGCT      60

CCAGGTCTCA AGTGATCCCC CTACCTCCGC CTCCCAAAGT TGTGGGATTG TAGGCATGAG     120

CCACTGCAAG AAAACCTTAA CTGCAGCCTA ATAATTGTTT TCTTTGGGAT AACTTTTAAA     180

GTACATTAAA AGACTATCAA CTTAATTTCT GATCATATTT TGTTGAATAA AATAAGTAAA     240

ATGTCTTGTG AACAAAATGC TTTTTAACAT CCATATAAAG CTATCTATAT ATAGCTATCT     300

ATGTCTATAT AGCTATTTTT TTTAACTTCC TTTTATTTTC CTTACAG                   347
```

(2) INFORMATION FOR SEQ ID NO:2:

(i) SEQUENCE CHARACTERISTICS:
       (A) LENGTH: 444 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:2:

```
GTAAGTCTGC CAGCATTATG AAAGTGAATC TTACTTTTGT AAAACTTTAT GGTTTGTGGA      60
```

```
AAACAAATGT TTTTGAACAG TTAAAAAGTT CAGATGTTAA AAAGTTGAAA GGTTAATGTA      120

AAACAATCAA TATTAAAGAA TTTTGATGCC AAAACTATTA GATAAAAGGT TAATCTACAT      180

CCCTACTAGA ATTCTCATAC TTAACTGGTT GGTTATGTGG AAGAAACATA CTTTCACAAT      240

AAAGAGCTTT AGGATATGAT GCCATTTTAT ATCACTAGTA GGCAGACCAG CAGACTTTTT      300

TTTATTGTGA TATGGGATAA CCTAGGCATA CTGCACTGTA CACTCTGACA TATGAAGTGC      360

TCTAGTCAAG TTTAACTGGT GTCCACAGAG GACATGGTTT AACTGGAATT CGTCAAGCCT      420

CTGGTTCTAA TTTCTCATTT GCAG                                            444

(2) INFORMATION FOR SEQ ID NO:3:

(i) SEQUENCE CHARACTERISTICS:
        (A) LENGTH: 347 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

AATTTTTAAA TTTTTTGTAG AGACAGGGTC TCATTATGTT GCCCAGGGTG GTGTCAAGCT       60

CCAGGTCTCA AGTGATCCCC CTACCTCCGC CTCCCAAAGT TGTGGGATTG TAGGCATGAG      120

CCACTGCAAG AAAACCTTAA CTGCAGCCTA ATAATTGTTT TCTTTGGGAT AACTTTTAAA      180

GTACATTAAA AGACTATCAA CTTAATTTCT GATCATATTT TGTTGAATAA AATAAGTAAA      240

ATGTCTTGTG AACAAAATGC TTTTTAACAT CCATATAAAG CTATCTATAT ATAGCTATCT      300

ATATCTATAT AGCTATTTTT TTTAACTTCC TTTTATTTTC CTTACAG                   347

(2) INFORMATION FOR SEQ ID NO:4:

(i) SEQUENCE CHARACTERISTICS:
        (A) LENGTH: 444 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

GTAAGTCTGC CAGCATTATG AAAGTGAATC TTACTTTTGT AAAACTTTAT GGTTTGTGGA       60

AAACAAATGT TTTTGAACAG TTAAAAAGTT CAGATGTTAG AAAGTTGAAA GGTTAATGTA      120

AAACAATCAA TATTAAAGAA TTTTGATGCC AAAACTATTA GATAAAAGGT TAATCTACAT      180

CCCTACTAGA ATTCTCATAC TTAACTGGTT GGTTGTGTGG AAGAAACATA CTTTCACAAT      240

AAAGAGCTTT AGGATATGAT GCCATTTTAT ATCACTAGTA GGCAGACCAG CAGACTTTTT      300

TTTATTGTGA TATGGGATAA CCTAGGCATA CTGCACTGTA CACTCTGACA TATGAAGTGC      360

TCTAGTCAAG TTTAACTGGT GTCCACAGAG GACATGGTTT AACTGGAATT CGTCAAGCCT      420

CTGGTTCTAA TTTCTCATTT GCAG                                            444

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"
```

(xi) SEQUENCE DESCRIPTION: SEQ ID NO:5:

AGACTATCAA CTTAATTTCT GATCA                                                         25

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:6:

TAAGGAATGT GAGCACCTTC CTTC                                                          24

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:7:

GTAATAACCA AATGCAATGT GAA                                                           23

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:8:

CTACAACACC CTTCTCACAG                                                               20

(2) INFORMATION FOR SEQ ID NO:9:

(i) SEQUENCE CHARACTERISTICS:
        (A) LENGTH: 294 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
                20                  25                  30

Ile Trp Asp Asp Thr Ala Leu Ile Lys Ala Tyr Asp Lys Ala Val Ala
            35                  40                  45

Ser Phe Lys His Ala Leu Lys Asn Gly Asp Ile Cys Glu Thr Ser Gly
        50                  55                  60

Lys Pro Lys Thr Thr Pro Lys Arg Lys Pro Ala Lys Lys Asn Lys Ser

```
                65                   70                    75                    80
Gln Lys Lys Asn Thr Ala Ala Ser Leu Gln Gln Trp Lys Val Gly Asp
                        85                    90                    95
Lys Cys Ser Ala Ile Trp Ser Glu Asp Gly Cys Ile Tyr Pro Ala Thr
                100                  105                   110
Ile Ala Ser Ile Asp Phe Lys Arg Glu Thr Cys Val Val Val Tyr Thr
                115                  120                   125
Gly Tyr Gly Asn Arg Glu Glu Gln Asn Leu Ser Asp Leu Leu Ser Pro
            130                  135                  140
Ile Cys Glu Val Ala Asn Asn Ile Glu Gln Asn Ala Gln Glu Asn Glu
145                 150                  155                  160
Asn Glu Ser Gln Val Ser Thr Asp Glu Ser Glu Asn Ser Arg Ser Pro
                165                  170                  175
Gly Asn Lys Ser Asp Asn Ile Lys Pro Lys Ser Ala Pro Trp Asn Ser
                180                  185                  190
Phe Leu Pro Pro Pro Pro Pro Met Pro Gly Pro Arg Leu Gly Pro Gly
            195                  200                  205
Lys Pro Gly Leu Lys Phe Asn Gly Pro Pro Pro Pro Pro Pro Pro Pro
210                 215                  220
Pro Pro His Leu Leu Ser Cys Trp Leu Pro Pro Phe Pro Ser Gly Pro
225                 230                  235                  240
Pro Ile Ile Pro Pro Pro Pro Ile Cys Pro Asp Ser Leu Asp Asp
                245                  250                  255
Ala Asp Ala Leu Gly Ser Met Leu Ile Ser Trp Tyr Met Ser Gly Tyr
            260                  265                  270
His Thr Gly Tyr Tyr Met Gly Phe Arg Gln Asn Gln Lys Glu Gly Arg
            275                  280                  285
Cys Ser His Ser Leu Asn
    290

(2) INFORMATION FOR SEQ ID NO:10:

(i) SEQUENCE CHARACTERISTICS:
        (A) LENGTH: 1582 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

CGGGGCCCCA CGCTGCGCAC CCGCGGGTTT GCTATGGCGA TGAGCAGCGG CGGCAGTGGT    60

GGCGGCGTCC CGGAGCAGGA GGATTCCGTG CTGTTCCGGC GCGGCACAGG CCAGAGCGAT   120

GATTCTGACA TTTGGGATGA TACAGCACTG ATAAAAGCAT ATGATAAAGC TGTGGCTTCA   180

TTTAAGCATG CTCTAAAGAA TGGTGACATT TGTGAAACTT CGGGTAAACC AAAAACCACA   240

CCTAAAAGAA AACCTGCTAA GAAGAATAAA AGCCAAAAGA AGAATACTGC AGCTTCCTTA   300

CAACAGTGGA AAGTTGGGGA CAAATGTTCT GCCATTTGGT CAGAAGACGG TTGCATTTAC   360

CCAGCTACCA TTGCTTCAAT TGATTTTAAG AGAGAAACCT GTGTTGTGGT TTACACTGGA   420

TATGGAAATA GAGAGGAGCA AAATCTGTCC GATCTACTTT CCCCAATCTG TGAAGTAGCT   480

AATAATATAG AACAGAATGC TCAAGAGAAT GAAAATGAAA GCCAAGTTTC AACAGATGAA   540

AGTGAGAACT CCAGGTCTCC TGGAAATAAA TCAGATAACA TCAAGCCCAA ATCTGCTCCA   600

TGGAACCCCT TTCTCCCTCC ACCACCCCCC ATGCCAGGGC CAAGACTGGG ACCAGGAAAG   660
```

-continued

```
CCAGGTCTAA AATTCAATGG CCCACCACCG CCACCGCCAC CACCACCACC CCACTTACTA      720

TCATGCTGGC TGCCTCCATT TCCTTCTGGA CCACCAATAA TTCCCCCACC ACCTCCCATA      780

TGTCCAGATT CTCTTGATGA TGCTGATGCT TTGGGAAGTA TGTTAATTTC ATGGTACATG      840

AGTGGCTATC ATACTGGCTA TTATATGGGT TTTAGACAAA ATCAAAAAGA AGGAAGGTGC      900

TCACATTCCT TAAATTAAGG AGAAATGCTG GCATAGAGCA GCACTAAATG ACACCACTAA      960

AGAAACGATC AGACAGATCT GGAATGTGAA GCGTTATAGA AGATAACTGG CCTCATTTCT     1020

TCAAAATATC AAGTGTTGGG AAAGAAAAAA GGAAGTGGAA TGGGTAACTC TTCTTGATTA     1080

AAAGTTATGT AATAACCAAA TGCAATGTGA ATATTTTAC TGGACTCTTT TGAAAAACCA      1140

TCTGTAAAAG ACTGAGGTGG GGGTGGGAGG CCAGCACGGT GGTGAGGCAG TTGAGAAAAT     1200

TTGAATGTGG ATTAGATTTT GAATGATATT GGATAATTAT TGGTAATTTT ATGGCCTGTG     1260

AGAAGGGTGT TGTAGTTTAT AAAAGACTGT CTTAATTTGC ATACTTAAGC ATTTAGGAAT     1320

GAAGTGTTAG AGTGTCTTAA AATGTTTCAA ATGGTTTAAC AAAATGTATG TGAGGCGTAT     1380

GTGGCAAAAT GTTACAGAAT CTAACTGGTG GACATGGCTG TTCATTGTAC TGTTTTTTTC     1440

TATCTTCTAT ATGTTTAAAA GTATATAATA AAAATATTTA ATTTTTTTTT AAAAAAAAAA     1500

AAAAAAAAAA AAAAAAAAAA AAAAAAAAAA AAAAAAAAAA AAAAAAAAAA AAAAAAAAAA     1560

AAAAAAAAAA AAAAAAAAA AA                                              1582

(2) INFORMATION FOR SEQ ID NO:11:

(i) SEQUENCE CHARACTERISTICS:
        (A) LENGTH: 1408 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

AATTTTTAAA TTTTTTGTAG AGACAGGGTC TCATTATGTT GCCCAGGGTG GTGTCAAGCT       60

CCAGGTCTCA AGTGATCCCC CTACCTCCGC CTCCCAAAGT TGTGGGATTG TAGGCATGAG      120

CCACTGCAAG AAAACCTTAA CTGCAGCCTA ATAATTGTTT TCTTTGGGAT AACTTTTAAA      180

GTACATTAAA AGACTATCAA CTTAATTTCT GATCATATTT TGTTGAATAA AATAAGTAAA      240

ATGTCTTGTG AACAAAATGC TTTTTAACAT CCATATAAAG CTATCTATAT ATAGCTATCT      300

ATATCTATAT AGCTATTTTT TTTAACTTCC TTTTATTTTC CTTACAGGGT TTTAGACAAA      360

ATCAAAAAGA AGGAAGGTGC TCACATTCCT TAAATTAAGG AGTAAGTCTG CCAGCATTAT      420

GAAAGTGAAT CTTACTTTTG TAAAACTTTA TGGTTTGTGG AAAACAAATG TTTTTGAACA      480

GTTAAAAAGT TCAGATGTTA GAAAGTTGAA AGGTTAATGT AAAACAATCA ATATTAAAGA      540

ATTTTGATGC CAAAACTATT AGATAAAAGG TTAATCTACA TCCCTACTAG AATTCTCATA      600

CTTAACTGGT TGGTTGTGTG GAAGAAACAT ACTTTCACAA TAAAGAGCTT TAGGATATGA      660

TGCCATTTTA TATCACTAGT AGGCAGACCA GCAGACTTTT TTTTATTGTG ATATGGGATA      720

ACCTAGGCAT ACTGCACTGT ACACTCTGAC ATATGAAGTG CTCTAGTCAA GTTTAACTGG      780

TGTCCACAGA GGACATGGTT TAACTGGAAT TCGTCAAGCC TCTGGTTCTA ATTTCTCATT      840

TGCAGGAAAT GCTGGCATAG AGCAGCACTA AATGACACCA CTAAAGAAAC GATCAGACAG      900

ATCTGGAATG TGAAGCGTTA TAGAAGATAA CTGGCCTCAT TTCTTCAAAA TATCAAGTGT      960

TGGGAAAGAA AAAAGGAAGT GGAATGGGTA ACTCTTCTTG ATTAAAAGTT ATGTAATAAC     1020
```

-continued

```
CAAATGCAAT GTGAAATATT TTACTGGACT CTTTTGAAAA ACCATCTGTA AAAGACTGAG    1080

GTGGGGGTGG GAGGCCAGCA CGGTGGTGAG GCAGTTGAGA AAATTTGAAT GTGGATTAGA    1140

TTTTGAATGA TATTGGATAA TTATTGGTAA TTTTATGGCC TGTGAGAAGG GTGTTGTAGT    1200

TTATAAAAGA CTGTCTTAAT TTGCATACTT AAGCATTTAG GAATGAAGTG TTAGAGTGTC    1260

TTAAAATGTT TCAAATGGTT TAACAAAATG TATGTGAGGC GTATGTGGCA AAATGTTACA    1320

GAATCTAACT GGTGGACATG GCTGTTCATT GTACTGTTTT TTTCTATCTT CTATATGTTT    1380

AAAAGTATAT AATAAAAATA TTTAATTT                                       1408
```

(2) INFORMATION FOR SEQ ID NO:12:

(i) SEQUENCE CHARACTERISTICS:
        (A) LENGTH: 1582 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

```
CGGGGCCCCA CGCTGCGCAT CCGCGGGTTT GCTATGGCGA TGAGCAGCGG CGGCAGTGGT      60

GGCGGCGTCC CGGAGCAGGA GGATTCCGTG CTGTTCCGGC GCGGCACAGG CCAGAGCGAT     120

GATTCTGACA TTTGGGATGA TACAGCACTG ATAAAAGCAT ATGATAAAGC TGTGGCTTCA     180

TTTAAGCATG CTCTAAAGAA TGGTGACATT TGTGAAACTT CGGGTAAACC AAAAACCACA     240

CCTAAAAGAA AACCTGCTAA GAAGAATAAA AGCCAAAAGA GAATACTGC AGCTTCCTTA      300

CAACAGTGGA AAGTTGGGGA CAAATGTTCT GCCATTTGGT CAGAAGACGG TTGCATTTAC     360

CCAGCTACCA TTGCTTCAAT TGATTTTAAG AGAGAAACCT GTGTTGTGGT TTACACTGGA     420

TATGGAAATA GAGAGGAGCA AAATCTGTCC GATCTACTTT CCCCAATCTG TGAAGTAGCT     480

AATAATATAG AACAGAATGC TCAAGAGAAT GAAAATGAAA GCCAAGTTTC AACAGATGAA     540

AGTGAGAACT CCAGGTCTCC TGGAAATAAA TCAGATAACA TCAAGCCCAA ATCTGCTCCA     600

TGGAACTCTT TTCTCCCTCC ACCACCCCCC ATGCCAGGGC AAGACTGGG ACCAGGAAAG      660

CCAGGTCTAA AATTCAATGG CCCACCACCG CCACCGCCAC CACCACCACC CCACTTACTA     720

TCATGCTGGC TGCCTCCATT TCCTTCTGGA CCACCAATAA TTCCCCCACC ACCTCCCATA     780

TGTCCAGATT CTCTTGATGA TGCTGATGCT TTGGGAAGTA TGTTAATTTC ATGGTACATG     840

AGTGGCTATC ATACTGGCTA TTATATGGGT TTCAGACAAA ATCAAAAAGA AGGAAGGTGC     900

TCACATTCCT TAAATTAAGG AGAAATGCTG GCATAGAGCA GCACTAAATG ACACCACTAA     960

AGAAACGATC AGACAGATCT GGAATGTGAA GCGTTATAGA AGATAACTGG CCTCATTTCT    1020

TCAAAATATC AAGTGTTGGG AAAGAAAAAA GGAAGTGGAA TGGGTAACTC TTCTTGATTA    1080

AAAGTTATGT AATAACCAAA TGCAATGTGA AATATTTTAC TGGACTCTTT TGAAAAACCA    1140

TCTGTAAAAG ACTGGGGTGG GGGTGGGAGG CCAGCACGGT GGTGAGGCAG TTGAGAAAAT    1200

TTGAATGTGG ATTAGATTTT GAATGATATT GGATAATTAT TGGTAATTTT ATGGCCTGTG    1260

AGAAGGGTGT TGTAGTTTAT AAAAGACTGT CTTAATTTGC ATACTTAAGC ATTTAGGAAT    1320

GAAGTGTTAG AGTGTCTTAA AATGTTTCAA ATGGTTTAAC AAAATGTATG TGAGGCGTAT    1380

GTGGCAAAAT GTTACAGAAT CTAACTGGTG GACATGGCTG TTCATTGTAC TGTTTTTTTC    1440

TATCTTCTAT ATGTTTAAAA GTATATAATA AAAATATTTA ATTTTTTTTT AAAAAAAAA    1500

AAAAAAAAAA AAAAAAAAA AAAAAAAAA AAAAAAAAA AAAAAAAAA AAAAAAAAA        1560
```

```
AAAAAAAAAA AAAAAAAAAA AA                                                    1582

(2) INFORMATION FOR SEQ ID NO:13:

(i) SEQUENCE CHARACTERISTICS:
        (A) LENGTH: 1408 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

AATTTTTAAA TTTTTTGTAG AGACAGGGTC TCATTATGTT GCCCAGGGTG GTGTCAAGCT        60

CCAGGTCTCA AGTGATCCCC CTACCTCCGC CTCCCAAAGT TGTGGGATTG TAGGCATGAG       120

CCACTGCAAG AAAACCTTAA CTGCAGCCTA ATAATTGTTT TCTTTGGGAT AACTTTTAAA       180

GTACATTAAA AGACTATCAA CTTAATTTCT GATCATATTT TGTTGAATAA AATAAGTAAA       240

ATGTCTTGTG AACAAAATGC TTTTTAACAT CCATATAAAG CTATCTATAT ATAGCTATCT       300

ATGTCTATAT AGCTATTTTT TTTAACTTCC TTTTATTTTC CTTACAGGGT TTCAGACAAA       360

ATCAAAAAGA AGGAAGGTGC TCACATTCCT TAAATTAAGG AGTAAGTCTG CCAGCATTAT       420

GAAAGTGAAT CTTACTTTTG TAAAACTTTA TGGTTTGTGG AAAACAAATG TTTTTGAACA       480

GTTAAAAAGT TCAGATGTTA AAAGTTGAAA AGGTTAATGT AAAACAATCA ATATTAAAGA       540

ATTTTGATGC CAAAACTATT AGATAAAAGG TTAATCTACA TCCCTACTAG AATTCTCATA       600

CTTAACTGGT TGGTTATGTG GAAGAAACAT ACTTTCACAA TAAAGAGCTT TAGGATATGA       660

TGCCATTTTA TATCACTAGT AGGCAGACCA GCAGACTTTT TTTTATTGTG ATATGGGATA       720

ACCTAGGCAT ACTGCACTGT ACACTCTGAC ATATGAAGTG CTCTAGTCAA GTTTAACTGG       780

TGTCCACAGA GGACATGGTT TAACTGGAAT TCGTCAAGCC TCTGGTTCTA ATTTCTCATT       840

TGCAGGAAAT GCTGGCATAG AGCAGCACTA AATGACACCA CTAAAGAAAC GATCAGACAG       900

ATCTGGAATG TGAAGCGTTA TAGAAGATAA CTGGCCTCAT TTCTTCAAAA TATCAAGTGT       960

TGGGAAAGAA AAAAGGAAGT GGAATGGGTA ACTCTTCTTG ATTAAAAGTT ATGTAATAAC      1020

CAAATGCAAT GTGAAATATT TTACTGGACT CTTTTGAAAA ACCATCTGTA AAAGACTGGG      1080

GTGGGGGTGG GAGGCCAGCA CGGTGGTGAG GCAGTTGAGA AAATTTGAAT GTGGATTAGA      1140

TTTTGAATGA TATTGGATAA TTATTGGTAA TTTTATGGCC TGTGAGAAGG GTGTTGTAGT      1200

TTATAAAGA CTGTCTTAAT TTGCATACTT AAGCATTTAG GAATGAAGTG TTAGAGTGTC      1260

TTAAAATGTT TCAAATGGTT TAACAAAATG TATGTGAGGC GTATGTGGCA AAATGTTACA      1320

GAATCTAACT GGTGGACATG GCTGTTCATT GTACTGTTTT TTTCTATCTT CTATATGTTT      1380

AAAAGTATAT AATAAAAATA TTTAATTT                                        1408

(2) INFORMATION FOR SEQ ID NO:14:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:14:

ACCTGANCCC AGANGGTCAAG GCTGCAGTG AGACGAGATT GCNCCACTGC CCTCCACCCT        60
```

```
GGGTGATAAG AGTGGGACCC TGTNTCAAAA CATACACACA CACACACACA CACACACACA        120

CACACACACA CACACTCTCT CTCTCTCTCT CTCTCTCTCT CTCTCTCTCT CTCTCTCTCA        180

AAAACACTTG GTCTGTTATT TTTNCGAAAT TGTCAGTCAT AGTTATCTGT TAGACCAAAG        240

CTGNGTAAGN ACATTTATTA CATTGCCTCC TACAACTTCA TCAGCTAATG TATTTGCTAT        300

ATAGCAATTA CATATNGGNA TATATTATCT TNAGGGGATG GCCANGTNAT AAAACTGTCA        360

CTGAGGAAAG GA    372
```

(2) INFORMATION FOR SEQ ID NO:15:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:15:

```
CCTCCCACCT NAGCCTCCCC AGTAGCTAGG ACTATAGGCG TGCNCCACCA AGCTCAGCTA         60

TTTTTNNTAT TTAGTAGAGA CGGGGTTTCG GCANGCTTAG GCCTCGTNTC GAACTCCAGT        120

GTGTGTGTGT GTGTGTGTGT GTGTGTGTGT GTGTGTGTGT GTGTGTGTGT AGATATTTAT        180

TCCCCCTCCC CCTTGGAAAA GTAAGTAAGC TCCTACTAGG AATTTAAAAC CTGCTTGATC        240

TATATAAAGA CAAACAAGGA AAGACAAACA TGGGGGCAGG AAGGAAGGCA GATC              294
```

(2) INFORMATION FOR SEQ ID NO:16:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:16:

```
TCGAGGTAGA TTTGTATTAT ATCCCATGTA CACACACACA CACACACACA CACACACACA         60

CACACACAGA CTTAATCTGT TTACAGAAAT AAAAGGAATA AAATACCGTT TCTACTATAC        120

ACCAAAACTA GCCATCTTGA C                                                  141
```

(2) INFORMATION FOR SEQ ID NO:17:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:17:

```
CCCTGAGAAG GCTTCCTCCT GAGTATGCAT AAACATTCAC AGCTTGCATG CGTGTGTGTG         60

TGTGTGTGTG TGTGTATGTT TGCTTGCACT GTAAAAACAA TTGCAACATC AACAGAAATA        120

AAAATTAAAG GAATAATTCT CCTCCGACTC TGCCGTTCCA TCCAGTGAAA CTCTTCATTC        180

TGGGGTAAAG TTCCTTCAGT TCTTTCATAG ATAGGTATAT ACTTCATAAG TCAAACAATC        240

AGGCTGGGTG CAGTAGCTCA TGCCTGTAAT CCCAGCCCTT TGGGAGGCCG AGCTGGGCAG        300
```

```
ATCGA                                                                      305

(2) INFORMATION FOR SEQ ID NO:18:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:18:

TCCACCCGCC TTGGCCTCCC AAAGCNCTGG GATTACAGGC GTGACTGCCG CACCCAGCTG      60

TAAACTGGNT TNNTAATGGT AGATTTTNAG GTATTAACAA TAGATAAAAA GATACTTTTN    120

GGCATACTGT GTATTGGGAT GGGGTTAGAA CAGGTGTNCT ACCCAAGACA TTTACTTAAA    180

ATCGCCCTCG AAATGCTATG TGAGCTGTGT GTGTGTGTGT GTGTGTGTGT GTATTAAGGA    240

AAAGCATGAA AGTATTTATG CTTGATTTTT TTTTTTNACT CATAGCTTCA TAGTGGANCA    300

GATACATAGT CTAAATCAAA ATGTTTAAAC TTTTTATGTC ACTTGCTGTC               350

(2) INFORMATION FOR SEQ ID NO:19:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Met Ala Met Ser Ser Gly Gly Ser Gly Gly Gly Val Pro Glu Gln Glu
1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
```

```
                195                 200                     205
Lys Pro Gly Leu Lys Phe Asn Gly Pro Pro Pro Pro Pro Pro
        210                 215             220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met
            275
```

(2) INFORMATION FOR SEQ ID NO:20:

(i) SEQUENCE CHARACTERISTICS:
        (A) LENGTH: 885 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 18..881

(xi) SEQUENCE DESCRIPTION: SEQ ID NO:20:

```
CGGCGTGGTA GCAGGCC ATG GCG ATG GGC AGT GGC GGA GCG GGC TCC GAG        50
                  Met Ala Met Gly Ser Gly Gly Ala Gly Ser Glu
                   1               5                      10

CAG GAA GAT ACG GTG CTG TTC CGG CGT GGC ACC GGC CAG AGT GAT GAT        98
Gln Glu Asp Thr Val Leu Phe Arg Arg Gly Thr Gly Gln Ser Asp Asp
             15                  20                  25

TCT GAC ATT TGG GAT GAT ACA GCA TTG ATA AAA GCT TAT GAT AAA GCT       146
Ser Asp Ile Trp Asp Asp Thr Ala Leu Ile Lys Ala Tyr Asp Lys Ala
         30                  35                  40

GTG GCT TCC TTT AAG CAT GCT CTA AAG AAC GGT GAC ATT TGT GAA ACT       194
Val Ala Ser Phe Lys His Ala Leu Lys Asn Gly Asp Ile Cys Glu Thr
     45                  50                  55

CCA GAT AAG CCA AAA GGC ACA GCC AGA AGA AAA CCT GCC AAG AAG AAT       242
Pro Asp Lys Pro Lys Gly Thr Ala Arg Arg Lys Pro Ala Lys Lys Asn
 60                  65                  70                  75

AAA AGC CAA AAG AAG AAT GCC ACA ACT CCC TTG AAA CAG TGG AAA GTT       290
Lys Ser Gln Lys Lys Asn Ala Thr Thr Pro Leu Lys Gln Trp Lys Val
                 80                  85                  90

GGT GAC AAG TGT TCT GCT GTT TGG TCA GAA GAC GGC TGC ATT TAC CCA       338
Gly Asp Lys Cys Ser Ala Val Trp Ser Glu Asp Gly Cys Ile Tyr Pro
             95                 100                 105

GCT ACT ATT ACG TCC ATT GAC TTT AAG AGA GAA ACC TGT GTC GTG GTT       386
Ala Thr Ile Thr Ser Ile Asp Phe Lys Arg Glu Thr Cys Val Val Val
        110                 115                 120

TAT ACT GGA TAT GGA AAC AGA GAG GAG CAA AAC TTA TCT GAC CTA CTT       434
Tyr Thr Gly Tyr Gly Asn Arg Glu Glu Gln Asn Leu Ser Asp Leu Leu
    125                 130                 135

TCC CCG ACC TGT GAA GTA GCT AAT AGT ACA GAA CAG AAC ACT CAG GAG       482
Ser Pro Thr Cys Glu Val Ala Asn Ser Thr Glu Gln Asn Thr Gln Glu
140                 145                 150                 155

AAT GAA AGT CAA GTT TCC ACA GAC GAC AGT GAA CAC TCC TCC AGA TCG       530
Asn Glu Ser Gln Val Ser Thr Asp Asp Ser Glu His Ser Ser Arg Ser
                160                 165                 170

CTC AGA AGT AAA GCA CAC AGC AAG TCC AAA GCT GCT CCG TGG ACC TCA       578
```

```
Leu Arg Ser Lys Ala His Ser Lys Ser Lys Ala Ala Pro Trp Thr Ser
            175                 180                 185

TTT CTT CCT CCA CCA CCC CCA ATG CCA GGG TCA GGA TTA GGA CCA GGA         626
Phe Leu Pro Pro Pro Pro Pro Met Pro Gly Ser Gly Leu Gly Pro Gly
        190                 195                 200

AAG CCA GGT CTA AAA TTC AAC GGC CCG CCG CCG CCG CCT CCA CTA CCC         674
Lys Pro Gly Leu Lys Phe Asn Gly Pro Pro Pro Pro Pro Pro Leu Pro
    205                 210                 215

CCT CCC CCC TTC CTG CCG TGC TGG ATG CCC CCG TTC CCT TCA GGA CCA         722
Pro Pro Pro Phe Leu Pro Cys Trp Met Pro Pro Phe Pro Ser Gly Pro
220                 225                 230                 235

CCA ATA ATC CCG CCA CCC CCT CCC ATC TCT CCC GAC TGT CTG GAT GAC         770
Pro Ile Ile Pro Pro Pro Pro Pro Ile Ser Pro Asp Cys Leu Asp Asp
            240                 245                 250

ACT GAT GCC CTG GGC AGT ATG CTA ATC TCT TGG TAC ATG AGT GGC TAC         818
Thr Asp Ala Leu Gly Ser Met Leu Ile Ser Trp Tyr Met Ser Gly Tyr
        255                 260                 265

CAC ACT GGC TAC TAT ATG GGT TTC AGA CAA AAT AAA AAA GAA GGA AAG         866
His Thr Gly Tyr Tyr Met Gly Phe Arg Gln Asn Lys Lys Glu Gly Lys
    270                 275                 280

TGC TCA CAT ACA AAT TAAG                                                885
Cys Ser His Thr Asn
285
```

(2) INFORMATION FOR SEQ ID NO:21:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ala Met Gly Ser Gly Ala Gly Ser Glu Gln Glu Asp Thr Val
 1               5                  10                  15

Leu Phe Arg Arg Gly Thr Gly Gln Ser Asp Asp Ser Asp Ile Trp Asp
            20                  25                  30

Asp Thr Ala Leu Ile Lys Ala Tyr Asp Lys Ala Val Ala Ser Phe Lys
        35                  40                  45

His Ala Leu Lys Asn Gly Asp Ile Cys Glu Thr Pro Asp Lys Pro Lys
    50                  55                  60

Gly Thr Ala Arg Arg Lys Pro Ala Lys Asn Lys Ser Gln Lys Lys
65                  70                  75                  80

Asn Ala Thr Thr Pro Leu Lys Gln Trp Lys Val Gly Asp Lys Cys Ser
            85                  90                  95

Ala Val Trp Ser Glu Asp Gly Cys Ile Tyr Pro Ala Thr Ile Thr Ser
        100                 105                 110

Ile Asp Phe Lys Arg Glu Thr Cys Val Val Tyr Thr Gly Tyr Gly
    115                 120                 125

Asn Arg Glu Glu Gln Asn Leu Ser Asp Leu Leu Ser Pro Thr Cys Glu
    130                 135                 140

Val Ala Asn Ser Thr Glu Gln Asn Thr Gln Glu Asn Glu Ser Gln Val
145                 150                 155                 160

Ser Thr Asp Asp Ser Glu His Ser Ser Arg Ser Leu Arg Ser Lys Ala
                165                 170                 175

His Ser Lys Ser Lys Ala Ala Pro Trp Thr Ser Phe Leu Pro Pro Pro
            180                 185                 190
```

```
Pro Pro Met Pro Gly Ser Gly Leu Gly Pro Lys Pro Gly Leu Lys
        195                 200                 205

Phe Asn Gly Pro Pro Pro Pro Pro Leu Pro Pro Pro Pro Phe Leu
        210                 215                 220

Pro Cys Trp Met Pro Pro Phe Pro Ser Gly Pro Pro Ile Ile Pro Pro
225             230                 235                     240

Pro Pro Pro Ile Ser Pro Asp Cys Leu Asp Asp Thr Asp Ala Leu Gly
            245                 250                 255

Ser Met Leu Ile Ser Trp Tyr Met Ser Gly Tyr His Thr Gly Tyr Tyr
            260                 265                 270

Met Gly Phe Arg Gln Asn Lys Lys Glu Gly Lys Cys Ser His Thr Asn
        275                 280                 285
```

(2) INFORMATION FOR SEQ ID NO:22:

(i) SEQUENCE CHARACTERISTICS:
        (A) LENGTH: 3271 base pairs
        (B) TYPE: nucleic acid
        (C) STRANDEDNESS: Not Relevant
        (D) TOPOLOGY: linear (ii) MOLECULE TYPE: DNA (genomic)

(ix) FEATURE:
        (A) NAME/KEY: CDS
        (B) LOCATION: 104..184

(ix) FEATURE:
        (A) NAME/KEY: CDS
        (B) LOCATION: 364..435

(ix) FEATURE:
        (A) NAME/KEY: CDS
        (B) LOCATION: 637..756

(ix) FEATURE:
        (A) NAME/KEY: CDS
        (B) LOCATION: 921..1121

(ix) FEATURE:
        (A) NAME/KEY: CDS
        (B) LOCATION: 1265..1417

(ix) FEATURE:
        (A) NAME/KEY: CDS
        (B) LOCATION: 1605..1700

(ix) FEATURE:
        (A) NAME/KEY: CDS
        (B) LOCATION: 1810..1920

(ix) FEATURE:
        (A) NAME/KEY: CDS
        (B) LOCATION: 2214..2261

(xi) SEQUENCE DESCRIPTION: SEQ ID NO:22:

```
CCTCCCGGGC ACCGTACTGT TCCGCTCCCA GAAGCCCCGG GCGCCGGAAG TCGTCACTCT      60

TAAGAAGGGA CGGGGCCCCA CGCTGCGCAC CCGCGGGTTT GCT ATG GCG ATG AGC     115
                                                Met Ala Met Ser
                                                  1

AGC GGC GGC AGT GGT GGC GGC GTC CCG GAG CAG GAG GAT TCC GTG CTG     163
Ser Gly Gly Ser Gly Gly Gly Val Pro Glu Gln Glu Asp Ser Val Leu
  5              10                 15                     20

TTC CGG CGC GGC ACA GGC CAG GTGAGGTCGC AGCCAGTGCA GTCTCCCTAT         214
Phe Arg Arg Gly Thr Gly Gln
                25

TAGCGCTCTC AGCACCCTTC TTCCGGCCCA ACTCTCCTTC CGCAGTGTAA TTTTGTTATG    274
```

```
TGTGGATTAA GATGACTCTT GGTACTAACA TACATTTTCT GATTAAACCT ATCTGNACAT          334

GAGTTGTTTT TATTTCTTAC CCTTTCCAG AGC GAT GAT TCT GAC ATT TGG GAT            387
                                Ser Asp Asp Ser Asp Ile Trp Asp
                                 30                          35

GAT ACA GCA CTG ATA AAA GCA TAT GAT AAA GCT GTG GCT TCA TTT AAG            435
Asp Thr Ala Leu Ile Lys Ala Tyr Asp Lys Ala Val Ala Ser Phe Lys
         40                  45                  50

GTATGAAATG CTTGNTTAGT CGTTTTCTTA TTTTCTCGTT ATTCATTTGG AAAGGAATTG          495

ATAACATACG ATAAAGTGTT AAAGGTGCTT TCTGAGGTGA CGGAGCCTTG AGACTAGCTT          555

ATAGTAGTAA CTGGGTTATG TCGTGACTTT TATTCTGTGC ACCACCCTGT AACATGTACA          615

TTTTTATTCC TATTTTCGTA G CAT GCT CTA AAG AAT GGT GAC ATT TGT GAA           666
                        His Ala Leu Lys Asn Gly Asp Ile Cys Glu
                                     55                  60

ACT TCG GGT AAA CCA AAA ACC ACA CCT AAA AGA AAA CCT GCT AAG AAG            714
Thr Ser Gly Lys Pro Lys Thr Thr Pro Lys Arg Lys Pro Ala Lys Lys
             65                  70                  75

AAT AAA AGC CAA AAG AAG AAT ACT GCA GCT TCC TTA CAA CAG                    756
Asn Lys Ser Gln Lys Lys Asn Thr Ala Ala Ser Leu Gln Gln
         80                  85                  90

GTTATTTTAA AATGTTGAGG ATTTAACTTC AAAGGATGTC TCATTAGTCC TTATTTAATA          816

GTGTAAAATG TCTTTAACTG CCTGCAGGTC GATCAAAACG AGATGATAGT TTGCCCTCTT          876

CAAAAGAAAT GTGTGCATGT ATATATCTTT GATTTCTTTT GTAG TGG AAA GTT GGG           932
                                                Trp Lys Val Gly
                                                             95

GAC AAA TGT TCT GCC ATT TGG TCA GAA GAC GGT TGC ATT TAC CCA GCT            980
Asp Lys Cys Ser Ala Ile Trp Ser Glu Asp Gly Cys Ile Tyr Pro Ala
                100                 105                 110

ACC ATT GCT TCA ATT GAT TTT AAG AGA GAA ACC TGT GTT GTG GTT TAC           1028
Thr Ile Ala Ser Ile Asp Phe Lys Arg Glu Thr Cys Val Val Val Tyr
            115                 120                 125

ACT GGA TAT GGA AAT AGA GAG GAG CAA AAT CTG TCC GAT CTA CTT TCC           1076
Thr Gly Tyr Gly Asn Arg Glu Glu Gln Asn Leu Ser Asp Leu Leu Ser
        130                 135                 140

CCA ATC TGT GAA GTA GCT AAT AAT ATA GAA CAG AAT GCT CAA GAG               1121
Pro Ile Cys Glu Val Ala Asn Asn Ile Glu Gln Asn Ala Gln Glu
145                 150                 155

GTAAGGATAC AAAAAAAAAA AAATTCAATT TCTGGAAGCA GAGACTAGAT GAGAAACTGT         1181

TAAACAGTAT ACACCACCGA GGCATTAATT TTTTCTTAAT CACACCCTTA AACAAAAAC          1241

CTGCATATTT TTTCTTTTTA AAG AAT GAA AAT GAA AGC CAA GTT TCA ACA GAT         1294
                        Asn Glu Asn Glu Ser Gln Val Ser Thr Asp
                                    160                 165

GAA AGT GAG AAC TCC AGG TCT CCT GGA AAT AAA TCA GAT AAC ATC AAG           1342
Glu Ser Glu Asn Ser Arg Ser Pro Gly Asn Lys Ser Asp Asn Ile Lys
        170                 175                 180

CCC AAA TCT GCT CCA TGG AAC TCT TTT CTC CCT CCA CCA CCC CCC ATG           1390
Pro Lys Ser Ala Pro Trp Asn Ser Phe Leu Pro Pro Pro Pro Pro Met
185                 190                 195                 200

CCA GGG CCA AGA CTG GGA CCA GGA AAG GTAAACCTTC TATGAAAGTT                 1437
Pro Gly Pro Arg Leu Gly Pro Gly Lys
                205

TTCCAGAAAA TAGTTAATGT CGGGACATTT AACCTCTCTG TTAACTAATT TGTAGCTCTC         1497

CCACAAATAT TCTGGGTAAT TATTTTTATC CTTTTGGTTT TGAGTCCTTT TTATTCCTAT         1557

CATATTGAAA TTGGTAAGTT AATTTTCCTT TGAAATATTC CTTATAG CCA GGT CTA           1613
                                                    Pro Gly Leu
                                                            210
```

```
AAA TTC AAT GGC CCA CCA CCG CCA CCG CCA CCA CCA CCA CCC CAC TTA      1661
Lys Phe Asn Gly Pro Pro Pro Pro Pro Pro Pro Pro Pro Pro His Leu
            215                 220                 225

CTA TCA TGC TGG CTG CCT CCA TTT CCT TCT GGA CCA CCA GTAAGTAAAA       1710
Leu Ser Cys Trp Leu Pro Pro Phe Pro Ser Gly Pro Pro
        230                 235                 240

AAGAGTATAG GTTAGATTTT GCTTTCACAT ACAATTTGAT AATTACCAGA CTTTACTTTT    1770

TGTTTACTGG ATATAAACAA TATCTTTTTC TGTCTCCAG ATA ATT CCC CCA CCA      1824
                                           Ile Ile Pro Pro Pro
                                                       245

CCT CCC ATA TGT CCA GAT TCT CTT GAT GAT GCT GAT GCT TTG GGA AGT      1872
Pro Pro Ile Cys Pro Asp Ser Leu Asp Asp Ala Asp Ala Leu Gly Ser
            250                 255                 260

ATG TTA ATT TCA TGG TAC ATG AGT GGC TAT CAT ACT GGC TAT TAT ATG      1920
Met Leu Ile Ser Trp Tyr Met Ser Gly Tyr His Thr Gly Tyr Tyr Met
            265                 270                 275

GTAAGTAATC ACTCAGCATC TTTTCCTGAC AATTTTTTTG TAGTTATGTG ACTTTGTTTG    1980

GTAAATTTAT AAAATACTAC TTGAACTGCA GCCTAATAAT TGTTTTCTTT GGGATAACTT    2040

TTAAAGTACA TTAAAAGACT ATCAACTTAA TTTCTGATCA TATTTTGTTG AATAAAATAA    2100

GTAAAATGTC TTGTGAAACA AAATGCTTTT TAACATCCAT ATAAAGCTAT CTATATATAG    2160

CTATCTATGT CTATATAGCT ATTTTTTTTA ACTTCCTTTT ATTTTCCTTA CAG GGT       2216
                                                            Gly
TTC AGA CAA AAT CAA AAA GAA GGA AGG TGC TCA CAT TCC TTA AAT          2261
Phe Arg Gln Asn Gln Lys Glu Gly Arg Cys Ser His Ser Leu Asn
280                 285                 290

TAAGGAGTAA GTCTGCCAGC ATTATGAAAG TGAATCTTAC TTTTGTAAAA CTTTATGGTT    2321

TGTGGAAAAC AAATGTTTTT GAACAGTTAA AAAGTTCAGA TGTTAAAAAG TTGAAAGGTT    2381

AATGTAAAAC AATCAATATT AAAGAATTTT GATGCCAAAA CTATTAGATA AAAGGTTAAT    2441

CTACATCCCT ACTAGAATTC TCATACTTAA CTGGTTGGTT ATGTGGAAGA AACATACTTT    2501

CACAATAAAG AGCTTTAGGA TATGATGCCA TTTTATATCA CTAGTAGGCA GACCAGCAGA    2561

CTTTTTTTTA TTGTGATATG GGATAACCTA GGCATACTGC ACTGTACACT CTGACATATG    2621

AAGTGCTCTA GTCAAGTTTA ACTGGTGTCC ACAGAGGACA TGGTTTAACT GGAATTCGTC    2681

AAGCCTCTGG TTCTAATTTC TCATTTGCAG GAAATGCTGG CATAGAGCAG CACTAAATGA    2741

CACCACTAAA GAAACGATCA GACAGATCTG GAATGTGAAG CGTTATAGAA GATAACTGGC    2801

CTCATTTCTT CAAAATATCA AGTGTTGGGA AGAAAAAAG GAAGTGGAAT GGGTAACTCT     2861

TCTTGATTAA AAGTTATGTA ATAACCAAAT GCAATGTGAA ATATTTTACT GGACTCTTTT    2921

GAAAAACCAT CTAGTAAAAG ACTGGGGTGG GGGTGGGAGG CCAGCACGGT GGTGAGGCAG    2981

TTGAGAAAAT TTGAATGTGG ATTAGATTTT GAATGATATT GGATAATTAT TGGTAATTTT    3041

ATGGCCTGTG AGAAGGGTGT TGTAGTTTAT AAAAGACTGT CTTAATTTGC ATACTTAAGC    3101

ATTTAGGAAT GAAGTGTTAG AGTGTCTTAA AATGTTTCAA ATGGTTTAAC AAAATGTATG    3161

TGAGGCGTAT GTGGCAAAAT GTTACAGAAT CTAACTGGTG GACATGGCTG TTCATTGTAC    3221

TGTTTTTTTC TATCTTCTAT ATGTTTAAAA GTATATAATA AAAATATTTA               3271

(2) INFORMATION FOR SEQ ID NO:23:

(i) SEQUENCE CHARACTERISTICS:
        (A) LENGTH: 637 base pairs
        (B) TYPE: nucleic acid
        (C) STRANDEDNESS: single
```

```
            (D) TOPOLOGY: linear (ii) MOLECULE TYPE: DNA (genomic)

(xi) SEQUENCE DESCRIPTION: SEQ ID NO:23:

GATCTGCCTT CCTTCCTGCC CCCATGTTTG TCTTTCCTTG TTTGTCTTTA TATAGATCAA      60

GCAGGTTTTA AATTCCTAGT AGGAGCTTAC ATTTACTTTT CCAAGGGGGA GGGGGAATAA     120

ATATCTACAC ACACACACAC ACACACACCA CACTGGAGTT CGAGACGAGG CCTAAGCAAC     180

ATGCCGAAAC CCCGTCTCTA CTAAATACAA AAAATAGCTG AGCTTGGTGG CGCACGCCTA     240

TAGTCCTAGC TACTGGGGAG GCTGAGGTGG GAGGATCGCT TGAGCCCAAG AAGTCGAGGC     300

TGCAGTGAGC CGAGATCGCG CCGCTGCACT CCAGCCTGAG CGACAGGGCG AGGCTCTGTC     360

TCAAAACAAA CAAACAAAAA AAAAAAGGAA AGGAAATATA ACACAGTGAA ATGAAAGGAT     420

TGAGAGAAAT GAAAAATATA CACGCCACAA ATGTGGGAGG GCGATAACCA CTCGTAGAAA     480

GCGTGAGAAG TTACTACAAG CGGTCCTCCC GGGCACCGTA CTGTTCCGCT CCCAGAAGCC     540

CCGGGCGCCG GAAGTCGTCA CTCTTAAGAA GGGACGGGGC CCCACGCTGC GCACCCGCGG     600

GTTTGCTATG GCGATGAGCA GCGGCGGCAG TGGTGGC                             637

(2) INFORMATION FOR SEQ ID NO:24:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:24:

AGGGCGAGGC TCTGTCTCA                                                   19

(2) INFORMATION FOR SEQ ID NO:25:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:25:

CGGGAGGACC GCTTGTAGT                                                   19

(2) INFORMATION FOR SEQ ID NO:26:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:26:

GCCGGAAGTC GTCACTCTT                                                   19
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:27:

GGGTGCTGAG AGCGCTAATA                                                     20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:28:

TGTGTGGATT AAGATGACTC                                                     20

(2) INFORMATION FOR SEQ ID NO:29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:29:

CACTTTATCG TATGTTATC                                                      19

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:30:

CTGTGCACCA CCCTGTAACA TG                                                22

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:31:

AAGGACTAAT GAGACATCC                                                    19

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:32:

CGAGATGATA GTTTGCCCTC                                                   20

(2) INFORMATION FOR SEQ ID NO:33:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:33:

AGCTACTTCA CAGATTGGGG AAAG                                              24

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:34:

CTCATCTAGT CTCTGCTTCC                                                   20

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:35:

TGGATATGGA AATAGAGAGG GAGC                                              24

(2) INFORMATION FOR SEQ ID NO:36:

(i) SEQUENCE CHARACTERISTICS:
            (A) LENGTH: 22 base pairs

```
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:36:

CACCCTTATA ACAAAAACCT GC                                            22

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:37:

GAGAAAGGAG TTCCATGGAG CAG                                           23

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:38:

GAGAGGTTAA ATGTCCCGAC                                               20

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:39:

GTGAGAACTC CAGGTCTCCT GG                                            22

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:40:

TGAGTCTGTT TGACTTCAGG                                               20
```

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:41:

GAAGGAAATG GAGGCAGCCA GC                                  22

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:42:

TTTCTACCCA TTAGAATCTG G                                   21

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:43:

CCCCACTTAC TATCATGCTG GCTG                               24

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:44:

CCAGACTTTA CTTTTTGTTT ACTG                               24

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:45:

ATAGCCACTC ATGTACCATG A                                                         21

(2) INFORMATION FOR SEQ ID NO:46:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:46:

AAGAGTAATT TAAGCCTCAG ACAG                                                      24

(2) INFORMATION FOR SEQ ID NO:47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:47:

CTCCCATATG TCCAGATTCT CTTG                                                      24

(2) INFORMATION FOR SEQ ID NO:48:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:48:

AGACTATCAA CTTAATTTCT GATCA                                                     25

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (xi) SEQUENCE DESCRIPTION: SEQ ID NO:49:

TAAGGAATGT GAGCACCTTC CTTC                                                      24

(2) INFORMATION FOR SEQ ID NO:50:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:50:

AGACTATCAA CTTAATTTCT GATCA                                              25

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:51:

GTAAGATTCA CTTTCATAAT GCTG                                               24

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:52:

CTTTATGGTT TGTGGAAAAC A                                                  21

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:53:

GGCATCATAT CCTAAAGCTC                                                    20

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:54:

```
GTAATAACCA AATGCAATGT GAA                                                       23

(2) INFORMATION FOR SEQ ID NO:55:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:55:

CTACAACACC CTTCTCACAG                                                            20

(2) INFORMATION FOR SEQ ID NO:56:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:56:

GGTGTCCACA GAGGACATGG                                                            20

(2) INFORMATION FOR SEQ ID NO:57:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:57:

AAGAGTTAAC CCATTCCAGC TTCC                                                       24

(2) INFORMATION FOR SEQ ID NO:58:

(i) SEQUENCE CHARACTERISTICS:
         (A) LENGTH: 26 amino acids
         (B) TYPE: amino acid
         (D) TOPOLOGY: linear (ii) MOLECULE TYPE: protein (xi) SEQUENCE DESCRIPTION: SEQ ID NO:58:

Met Ala Met Ser Ser Gly Gly Ser Gly Gly Gly Val Pro Glu Gln Glu
 1               5                  10                  15

Asp Ser Val Leu Phe Arg Arg Gly Thr Gly
            20                  25

(2) INFORMATION FOR SEQ ID NO:59:

(i) SEQUENCE CHARACTERISTICS:
         (A) LENGTH: 24 amino acids
         (B) TYPE: amino acid
         (D) TOPOLOGY: linear
```

(ii) MOLECULE TYPE: protein (xi) SEQUENCE DESCRIPTION: SEQ ID NO:59:

Ser Asp Asp Ser Asp Ile Trp Asp Asp Thr Ala Leu Ile Lys Ala Tyr
1               5                   10                  15

Asp Lys Ala Val Ala Ser Phe Lys
            20

(2) INFORMATION FOR SEQ ID NO:60:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:60:

His Ala Leu Lys Asn Gly Asp Ile Cys Glu Thr Ser Gly Lys Pro Lys
1               5                   10                  15

Thr Thr Pro Lys Arg Lys Pro Ala Lys Lys Asn Lys Ser Gln Lys Lys
            20                  25                  30

Asn Thr Ala Ala Ser Leu Gln Gln
            35                  40

(2) INFORMATION FOR SEQ ID NO:61:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:61:

Trp Lys Val Gly Asp Lys Cys Ser Ala Ile Trp Ser Glu Asp Gly Cys
1               5                   10                  15

Ile Tyr Pro Ala Thr Ile Ala Ser Ile Asp Phe Lys Arg Glu Thr Cys
            20                  25                  30

Val Val Val Tyr Thr Gly Tyr Gly Asn Arg Glu Glu Gln Asn Leu Ser
            35                  40                  45

Asp Leu Leu Ser Pro Ile Cys Glu Val Ala Asn Asn Ile Glu Gln Asn
    50                  55                  60

Ala Gln Glu
65

(2) INFORMATION FOR SEQ ID NO:62:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:62:

Asn Glu Asn Glu Ser Gln Val Ser Thr Asp Glu Ser Glu Asn Ser Arg
1               5                   10                  15

Ser Pro Gly Asn Lys Ser Asp Asn Ile Lys Pro Lys Ser Ala Pro Trp
            20                  25                  30

Asn Ser Phe Leu Pro Pro Pro Pro Met Pro Gly Pro Arg Leu Gly
            35                  40                  45

```
Pro Gly Lys
    50

(2) INFORMATION FOR SEQ ID NO:63:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:63:

Pro Gly Leu Lys Phe Asn Gly Pro Pro Pro Pro Pro Pro Pro Pro
 1               5                  10                  15

Pro His Leu Leu Ser Cys Trp Leu Pro Pro Phe Pro Ser Gly Pro Pro
            20                  25                  30

(2) INFORMATION FOR SEQ ID NO:64:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:64:

Ile Ile Pro Pro Pro Pro Pro Ile Cys Pro Asp Ser Leu Asp Asp Ala
 1               5                  10                  15

Asp Ala Leu Gly Ser Met Leu Ile Ser Trp Tyr Met Ser Gly Tyr His
            20                  25                  30

Thr Gly Tyr Tyr Met
        35

(2) INFORMATION FOR SEQ ID NO:65:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:65:

Gly Phe Arg Gln Asn Gln Lys Glu Gly Arg Cys Ser His Ser Leu Asn
 1               5                  10                  15
```